(12) United States Patent
Steinhauer et al.

(10) Patent No.: US 9,687,618 B2
(45) Date of Patent: Jun. 27, 2017

(54) VENTILATION HARM INDEX

(75) Inventors: Tom Steinhauer, San Diego, CA (US);
Timothy Riddle, San Diego, CA (US);
Thomas George, Yorba Linda, CA
(US); Mark Rogers, Irvine, CA (US);
Glen Gee, Yorba Linda, CA (US)

(73) Assignee: CAREFUSION 207, INC., San Diego, CA (US)

( * ) Notice: Subject to any disclaimer, the term of this patent is extended or adjusted under 35 U.S.C. 154(b) by 797 days.

(21) Appl. No.: 13/288,013

(22) Filed: Nov. 2, 2011

(65) Prior Publication Data

US 2013/0104892 A1 May 2, 2013

(51) Int. Cl.
*A61M 16/00* (2006.01)
*G06F 19/00* (2011.01)

(52) U.S. Cl.
CPC ........ *A61M 16/00* (2013.01); *A61M 16/0051* (2013.01); *G06F 19/345* (2013.01); *G06F 19/3418* (2013.01); *G06F 19/3431* (2013.01); *A61M 2205/3375* (2013.01); *A61M 2205/3553* (2013.01); *A61M 2205/3561* (2013.01); *A61M 2205/3584* (2013.01); *A61M 2205/3592* (2013.01); *A61M 2205/505* (2013.01); *A61M 2205/52* (2013.01); *A61M 2205/60* (2013.01); *A61M 2205/609* (2013.01); *A61M 2205/6054* (2013.01); *A61M 2205/6072* (2013.01); *A61M 2209/01* (2013.01); *A61M 2230/205* (2013.01); *A61M 2230/62* (2013.01); *A61M 2230/63* (2013.01); *G06F 19/323* (2013.01); *G06F 19/3412* (2013.01)

(58) Field of Classification Search
CPC .. A61M 16/00; A61M 16/04; A61M 16/0003;
A61M 16/105; A61M 16/043; A61M 16/0463; A61M 16/0475; A61M 16/0477; A61M 16/0484; A61M 16/0486; A61M 16/0051; A61M 2016/0021; A61M 16/0027; A61M 16/0036; A61M 16/0039; A62B 7/00; A62B 9/006
USPC ............ 128/200.24, 202.22, 203.12, 203.14, 128/203.25, 204.18, 204.21–204.23, 128/203.11, 205.23
See application file for complete search history.

(56) References Cited

U.S. PATENT DOCUMENTS

| | | |
|---|---|---|
| 4,988,336 A | 1/1991 | Kohn |
| 5,065,315 A | 11/1991 | Garcia |
| 5,544,649 A | 8/1996 | David et al. |
| 5,626,151 A | 5/1997 | Linden |

(Continued)

FOREIGN PATENT DOCUMENTS

| | | |
|---|---|---|
| WO | WO-2011087111 A1 | 7/2011 |
| WO | WO-2013/067223 A1 | 5/2013 |

OTHER PUBLICATIONS

"Solutions," retrieved on Sep. 16, 2013, 1 page, Theronyx, retrieved from <http://www.theronyx.com/solutions>.

(Continued)

*Primary Examiner* — Peter S Vasat
*Assistant Examiner* — Ned T Heffner
(74) *Attorney, Agent, or Firm* — McDermott Will & Emery LLP

(57) ABSTRACT

A method for generating a ventilation harm index. The method includes accessing data from a plurality of ventilators in operation, analyzing an aggregate of the data, and generating the ventilation harm index based on the analyzed aggregated data.

11 Claims, 29 Drawing Sheets

(56) References Cited

U.S. PATENT DOCUMENTS

| | | | |
|---|---|---|---|
| 5,881,723 A * | 3/1999 | Wallace et al. | 128/204.21 |
| 5,931,160 A | 8/1999 | Gilmore et al. | |
| 5,987,519 A | 11/1999 | Peifer et al. | |
| 6,148,814 A | 11/2000 | Clemmer et al. | |
| 6,158,430 A | 12/2000 | Pfeiffer et al. | |
| 6,158,433 A | 12/2000 | Ong et al. | |
| 6,349,724 B1 | 2/2002 | Burton et al. | |
| 6,369,847 B1 | 4/2002 | James et al. | |
| 6,406,426 B1 | 6/2002 | Reuss et al. | |
| 6,459,933 B1 | 10/2002 | Lurie et al. | |
| 6,551,243 B2 | 4/2003 | Bocionek et al. | |
| 6,666,820 B1 * | 12/2003 | Poole | 600/300 |
| 6,839,753 B2 | 1/2005 | Biondi et al. | |
| 6,955,170 B1 | 10/2005 | Mullins et al. | |
| 7,165,221 B2 | 1/2007 | Monteleone et al. | |
| 7,225,809 B1 | 6/2007 | Bowen et al. | |
| 7,237,205 B2 * | 6/2007 | Sarel | 715/786 |
| 7,334,578 B2 | 2/2008 | Biondi et al. | |
| 7,395,216 B2 | 7/2008 | Rosenfeld et al. | |
| 7,677,246 B2 | 3/2010 | Kepler et al. | |
| 7,698,156 B2 | 4/2010 | Martucci et al. | |
| 8,015,972 B2 | 9/2011 | Pirzada | |
| 8,255,238 B2 | 8/2012 | Powell et al. | |
| 8,321,284 B2 | 11/2012 | Clements et al. | |
| 8,327,846 B2 | 12/2012 | Bowditch et al. | |
| 8,447,629 B2 | 5/2013 | Rappaport et al. | |
| 8,522,779 B2 | 9/2013 | Lee et al. | |
| 8,695,593 B2 | 4/2014 | Tehrani | |
| 2001/0016821 A1 | 8/2001 | DeBusk et al. | |
| 2001/0027791 A1 | 10/2001 | Wallace et al. | |
| 2002/0022973 A1 | 2/2002 | Sun et al. | |
| 2002/0026941 A1 | 3/2002 | Biondi et al. | |
| 2002/0077862 A1 | 6/2002 | Auer et al. | |
| 2002/0091309 A1 | 7/2002 | Auer | |
| 2002/0120676 A1 | 8/2002 | Biondi et al. | |
| 2002/0133061 A1 | 9/2002 | Manetta | |
| 2003/0050802 A1 | 3/2003 | Jay et al. | |
| 2003/0101076 A1 * | 5/2003 | Zaleski | 705/2 |
| 2004/0077934 A1 | 4/2004 | Massad | |
| 2004/0249675 A1 | 12/2004 | Stark et al. | |
| 2005/0108057 A1 | 5/2005 | Cohen et al. | |
| 2005/0137653 A1 | 6/2005 | Friedman et al. | |
| 2005/0151640 A1 | 7/2005 | Hastings | |
| 2005/0188083 A1 | 8/2005 | Biondi et al. | |
| 2005/0192845 A1 | 9/2005 | Brinsfield et al. | |
| 2005/0267348 A1 | 12/2005 | Wollenweber et al. | |
| 2005/0268916 A1 | 12/2005 | Mumford et al. | |
| 2006/0031095 A1 | 2/2006 | Barth et al. | |
| 2006/0162727 A1 | 7/2006 | Biondi et al. | |
| 2006/0174883 A1 | 8/2006 | Aylsworth et al. | |
| 2006/0180150 A1 | 8/2006 | Dittmann | |
| 2006/0206011 A1 | 9/2006 | Higgins et al. | |
| 2006/0289020 A1 * | 12/2006 | Tabak et al. | 128/898 |
| 2007/0005621 A1 | 1/2007 | Lesh et al. | |
| 2007/0015976 A1 | 1/2007 | Miesel et al. | |
| 2007/0023045 A1 | 2/2007 | Kwok et al. | |
| 2007/0033072 A1 | 2/2007 | Bildirici | |
| 2007/0276696 A1 | 11/2007 | Gauvin et al. | |
| 2007/0283958 A1 | 12/2007 | Naghavi | |
| 2008/0053438 A1 | 3/2008 | DeVries et al. | |
| 2008/0072902 A1 | 3/2008 | Setzer et al. | |
| 2008/0077436 A1 | 3/2008 | Muradia | |
| 2008/0086691 A1 | 4/2008 | Hopermann et al. | |
| 2008/0091466 A1 | 4/2008 | Butler et al. | |
| 2008/0097793 A1 | 4/2008 | Dicks et al. | |
| 2008/0097913 A1 | 4/2008 | Dicks et al. | |
| 2008/0140160 A1 | 6/2008 | Goetz et al. | |
| 2008/0230064 A1 | 9/2008 | Tham | |
| 2008/0271736 A1 | 11/2008 | Leonard et al. | |
| 2008/0288023 A1 | 11/2008 | John | |
| 2008/0308101 A1 | 12/2008 | Spandorfer | |
| 2008/0312548 A1 | 12/2008 | Hartley et al. | |
| 2009/0044803 A1 | 2/2009 | Garcia Fernandez | |
| 2009/0112160 A1 | 4/2009 | Yang | |
| 2009/0184823 A1 | 7/2009 | Tessier | |
| 2009/0229610 A1 | 9/2009 | Oates et al. | |
| 2009/0241956 A1 | 10/2009 | Baker, Jr. et al. | |
| 2009/0293886 A1 | 12/2009 | Dedrick et al. | |
| 2009/0326389 A1 | 12/2009 | Ralfs | |
| 2010/0071697 A1 | 3/2010 | Jafari et al. | |
| 2010/0078017 A1 | 4/2010 | Andrieux et al. | |
| 2010/0083968 A1 | 4/2010 | Wondka et al. | |
| 2010/0085156 A1 | 4/2010 | Tucker | |
| 2010/0108064 A1 | 5/2010 | Blackwell et al. | |
| 2010/0161345 A1 | 6/2010 | Cain et al. | |
| 2010/0288279 A1 | 11/2010 | Seiver et al. | |
| 2010/0298718 A1 | 11/2010 | Gilham et al. | |
| 2010/0318155 A1 | 12/2010 | Mahajan et al. | |
| 2011/0011400 A1 | 1/2011 | Gentner et al. | |
| 2011/0073107 A1 | 3/2011 | Rodman et al. | |
| 2011/0077970 A1 | 3/2011 | Mellin et al. | |
| 2011/0078253 A1 | 3/2011 | Chan et al. | |
| 2011/0087756 A1 | 4/2011 | Biondi et al. | |
| 2011/0108034 A1 | 5/2011 | Viertio-Oja | |
| 2011/0112442 A1 | 5/2011 | Meger et al. | |
| 2011/0120470 A1 | 5/2011 | Bowerbank | |
| 2011/0139155 A1 | 6/2011 | Farrell et al. | |
| 2011/0178373 A1 | 7/2011 | Pacey et al. | |
| 2011/0208539 A1 * | 8/2011 | Lynn | 705/2 |
| 2011/0231505 A1 | 9/2011 | Chan et al. | |
| 2011/0238441 A1 | 9/2011 | Callas | |
| 2011/0319322 A1 | 12/2011 | Bashan et al. | |
| 2012/0108984 A1 | 5/2012 | Bennett et al. | |
| 2012/0109240 A1 | 5/2012 | Zhou et al. | |
| 2012/0118285 A1 | 5/2012 | Wondka et al. | |
| 2012/0137250 A1 | 5/2012 | Milne et al. | |
| 2012/0145153 A1 | 6/2012 | Bassin et al. | |
| 2012/0216809 A1 | 8/2012 | Milne et al. | |
| 2012/0272955 A1 | 11/2012 | Cool et al. | |
| 2012/0330177 A1 | 12/2012 | Al-Rawas et al. | |
| 2013/0032147 A1 | 2/2013 | Robinson et al. | |
| 2013/0186405 A1 | 7/2013 | Krzyzanowski et al. | |
| 2013/0199533 A1 | 8/2013 | Steinhauer et al. | |
| 2014/0158124 A1 | 6/2014 | L'her et al. | |

OTHER PUBLICATIONS

Chipman, Daniel W., et al. "Performance comparison of 15 transport ventilators." Respiratory care 52.6 (2007): 740-751.

Fairley, H. Barrie, and B.A. Britt. "The adequacy of the air-mix control in ventilators operated from an oxygen source." Canadian Medical Association Journal 90.25 (1964): 1394.

Krieger, Bruce P., et al. "Initial experience with a central respiratory monitoring unit as a cost-saving alternative to the intensive care unit for Medicare patients who require long-term ventilator support." Chest Journal 93.2 (1988): 395-397.

Shimpi, A.L., "iphone 3GS Performance: A Significant Performance Bump," Anand Tech (2009), http://www.anandtech.com/show/2790.

Simonds, A. K. "Streamlining wearning: protocols and weaning units." Thorax 60.3 (2005): 175-182.

"Vital Sync Virtual Patient monitoring Platform 2.0," retrieved on Sep. 16, 2013, 2 pages, Covidien, retrieved from <http://www.covidien.com/RMS/pages.aspx?page+Product/Vital-Sync-Vitrual-Patient-Monitoring-Platform>.

Title: CPAP Equipment: CPAP Software Date Archived: May 12, 2012 Publisher: cpap.com.

"Medicare Quarterly Provider Compliance Newsletter", Oct. 2011, 21 pages, vol. 2, Issue 1, CMS.

"AVEA Ventilator Systems Operator's Manual", Cardinal Health, Sep. 1, 2008, pp. 1-244, XP055077133, Retrieved from the Internet: URL:http://www.frankshospitalworkshop.com/equipment/documents/ventilators/user_manuals/Cardinal_Health_avea_-_User_manual.pdf.

"Carefusion Announces New Ventilation Solution to Help Hospitals Provide improved Patient Care and Reduce Costs", Feb. 21, 2012, pp. 1-2, XP055077131, Retrieved from the Internet: URL:http://media.carefusion.com/index.php?s=32344&item=106634.

International Preliminary Report of Patentability for International Application No. PCT/US2012/063119, dated Feb. 27, 2014, 14 pages.

(56) References Cited

OTHER PUBLICATIONS

International Preliminary Report of Patentability for International Application No. PCT/US2013/048734, dated Dec. 31, 2014, 8 pages.
International Search Report and Written Opinion for International Application No. PCT/US2012/063119, dated Mar. 29, 2013, 8 pages.
International Search Report and Written Opinion for International Application No. PCT/US2013/048734, dated Sep. 9, 2013, 12 pages.
International Search Report for International Application No. PCT/US2013/057860, dated Nov. 7, 2013, 2 pages.
International Search Report for International Application No. PCT/US2013/057862, dated Dec. 12, 2013, 2 pages.
Extended European Search Report for Application No. 12844716.6, dated Jan. 4, 2016, 12 pages.
Govoni, et al., "An Improved Telemedicine System for Remote Titration and Optimization of Home Mechanical Ventilation", Biomedical Engineering Conference (CIBEC), 2010 5th Cairo International, IEEE, Dec. 16, 2010, pp. 66-69, XP031979754.

* cited by examiner

VENTILATION HARM INDEX

CROSS-REFERENCE TO RELATED U.S. APPLICATIONS

This Application is related to U.S. patent application Ser. No. 13/287,419, entitled, "Bi-Directional Ventilator Communication," by Steinhauer et al., with filing date Nov. 2, 2011, and assigned to the assignee of the present application.

This Application is related to U.S. patent application Ser. No. 13/287,490, entitled, "Contextualizing Ventilator Data," by Steinhauer et al., with filing date Nov. 2, 2011, and assigned to the assignee of the present application.

This Application is related to U.S. patent application Ser. No. 13/287,876, entitled, "Ventilator Component Module," by Steinhauer et al., with filing date Nov. 2, 2011, and assigned to the assignee of the present application.

This Application is related to U.S. patent application Ser. No. 13/287,935, entitled, "Automatic Implementation of a Ventilator Protocol," by Steinhauer et al., with filing date Nov. 2, 2011, and assigned to the assignee of the present application.

This Application is related to U.S. patent application Ser. No. 13/287,972, entitled, "Implementing Ventilator Rules on a Ventilator," by Steinhauer et al., with filing date Nov. 2, 2011, and assigned to the assignee of the present application.

This Application is related to U.S. patent application Ser. No. 13/287,572, entitled, "Healthcare Facility Ventilation Management," by Steinhauer et al., with filing date Nov. 2, 2011, and issued on Nov. 3, 2015 under U.S. Pat. No. 9,177,109, and assigned to the assignee of the present application.

This Application is related to U.S. patent application Ser. No. 13/287,752, entitled, "Wide Area Ventilation Management," by Steinhauer et al., with filing date Nov. 2, 2011, and assigned to the assignee of the present application.

This Application is related to U.S. patent application, Ser. No. 13/287,993, entitled, "Analyzing Medical Device Data," by Steinhauer et al., with filing date Nov. 2, 2011, and assigned to the assignee of the present application.

This Application is related to U.S. patent application Ser. No. 13/287,995, entitled, "Ventilator Report Generation," by Steinhauer et al., with filing date Nov. 2, 2011, and assigned to the assignee of the present application.

This Application is related to U.S. patent application Ser. No. 13/288,000, entitled, "Suggesting Ventilator Protocols," by Steinhauer et al., with filing date Nov. 2, 2011, and assigned to the assignee of the present application.

This Application is related to U.S. patent application Ser. No. 13/287,981, entitled, "Ventilator Avoidance Report," by Steinhauer et al., with filing date Nov. 2, 2011, and assigned to the assignee of the present application.

This Application is related to U.S. patent application Ser. No. 13/288,006, entitled, "Assisting Ventilator Documentation at a Point of Care," by Steinhauer et al., with filing date Nov. 2, 2011, and assigned to the assignee of the present application.

BACKGROUND

Typically, a ventilator includes a single direction of communication. For example, a ventilator is only able to send data outbound to another entity. Also, the communication is a wire line communication. Accordingly, the wire line single direction ventilator communication functionality is limited.

Moreover, several other aspects of a conventional ventilator are inefficient. As a result, work flow associated with the ventilator is inefficient and negatively affected.

The drawings referred to in this description should be understood as not being drawn to scale except if specifically noted.

DESCRIPTION OF EMBODIMENTS

Reference will now be made in detail to embodiments of the present technology, examples of which are illustrated in the accompanying drawings. While the technology will be described in conjunction with various embodiment(s), it will be understood that they are not intended to limit the present technology to these embodiments. On the contrary, the present technology is intended to cover alternatives, modifications and equivalents, which may be included within the spirit and scope of the various embodiments as defined by the appended claims.

Furthermore, in the following description of embodiments, numerous specific details are set forth in order to provide a thorough understanding of the present technology. However, the present technology may be practiced without these specific details. In other instances, well known methods, procedures, components, and circuits have not been described in detail as not to unnecessarily obscure aspects of the present embodiments.

Bi-Directional Ventilator Communication

Figure 1:
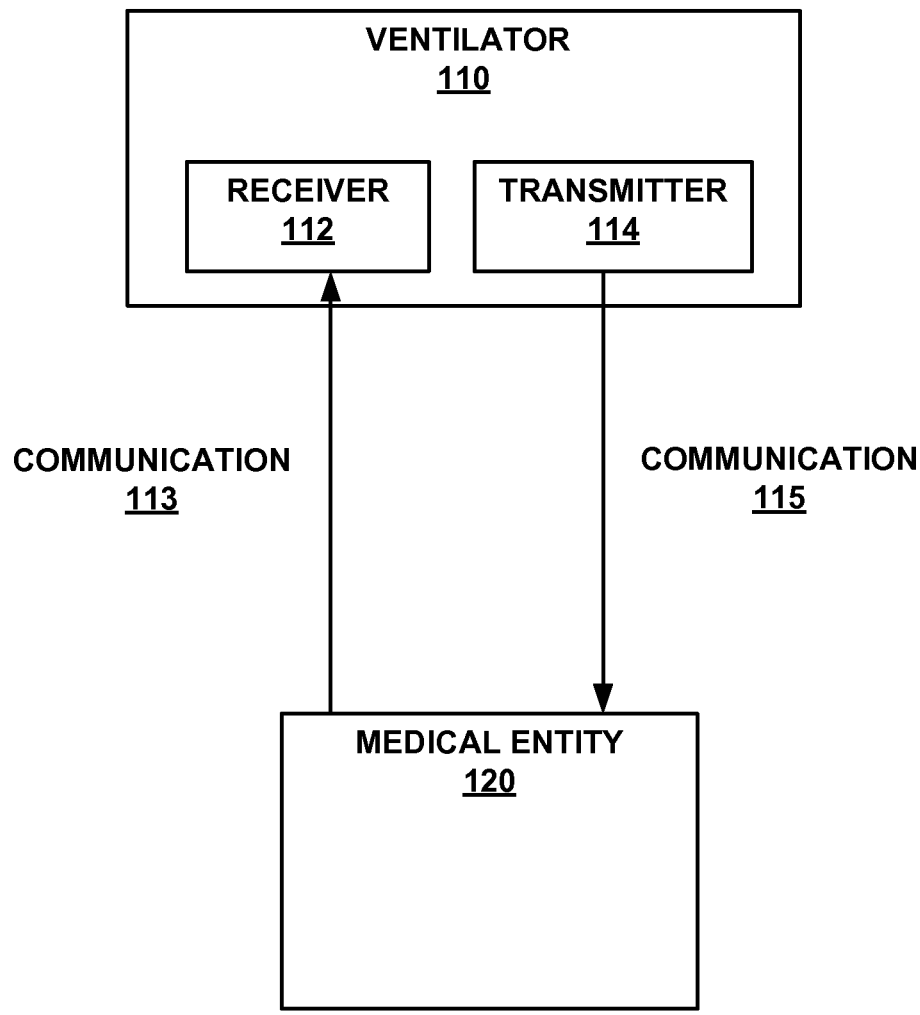
FIG. 1 illustrates an embodiment of a bi-directional communication system.

FIG. 1 depicts an embodiment of a bi-directional communication system 100. In various embodiments, the bi-directional communication is wired or wireless. System 100 includes ventilator 110 and medical entity 120. As depicted, ventilator 110 is able to bi-directionally communicate with medical entity 120. For example, ventilator 110 and medical entity 120 are able to communicate by receiving and transmitting information to one another. In various embodiments, system 100 can include one or more ventilators that are able to bi-directionally communicate with one or more medical entities or other ventilators.

Although system 100 depicts ventilator 110 that is able to bi-directionally communication with medical entity 120, it should be appreciated other medical devices may be able to bi-directionally communicate with medical entity 120. However, for clarity and brevity, the description below will primarily focus primarily on the structure and functionality of a ventilator.

In general, ventilator 110 can be any medical ventilator configured to provide the mechanism to move breathable air into and out of the lungs of a patient. For example, ventilator 110 can include a compressible air reservoir or turbine, air and oxygen supplies, a set of valves and tubes, and a patient circuit (not shown).

In particular, ventilator 110 also includes receiver 112 and transmitter 114. Receiver 112 is configured for receiving communication 113 from medical entity 120. Receiver 112 can be a wireless receiver configured for receiving a wireless communication.

Transmitter 114 is configured for transmitting communication 115 to medical entity 120 or to a plurality of different medical entities. Transmitter 114 can be a wireless transmitter for wirelessly transmitting a communication.

Communication 113, received by ventilator 110, can occur in a variety of forms. For example, communication 113 can include, instructions to stream ventilator information, instructions to provide a snapshot of ventilator information, remotely control ventilator 110, instructions to annotate ventilator information, etc.

In one embodiment, communication 113 is associated with ventilator manipulation. For example, communication 113 is associated with the manipulation of ventilator functionality (e.g., changing ventilator settings, etc.).

In some embodiments, communication 113 affects the functionality of ventilator 110. For example, communication 113 facilitates in the changing of configurations and/or ventilator settings of ventilator 110. Accordingly, communication 113 is not simply a request for ventilator information. As such, communication 113 is not required to be a request for ventilator information.

In one embodiment, communication 115 is transmitted to and stored in medical entity 120. Also, communication may be transmitted from ventilator 110 and stored separately from medical entity 120, for example, in a database or server.

In another embodiment, communication 115 is transmitted directly to medical entity 120. For example, communication is streaming data transmitted directly to a hand held device, which is discussed in further detail below. As such, communication 115 is not stored (or not required to be stored) in a database or server. In another embodiment, the hand held device does comprise server communication.

Medical entity 120 is any medical entity that is able to bi-directionally communicate with ventilator 110 (or other medical devices).

In one embodiment, medical entity 120 is a healthcare facility network. In general, a healthcare facility network is a network (or plurality of networks) that facilitates in the management and communication of information regarding medical devices and/or patient care. In regards to a healthcare facility, the bi-directional communication with ventilator 110 is wireless. For example, the wireless bi-directional communication can include 802.11/WiFi for communication with a LAN in the healthcare facility.

In another embodiment, medical entity 120 is wide area network (WAN). In such an embodiment, the bi-directional communication is wireless. For example, medical entity 120 may include a cellular modem to communicate with the WAN, for example, in a home healthcare environment. The WAN can also communicate with a healthcare facility network or a ventilator knowledge portal. It should be appreciated that the WAN can be set up by a third party vendor of ventilators.

In a further embodiment, medical entity is a hosted knowledge portal. As described in detail below, the hosted knowledge portal is a system that collects and aggregates ventilator information and also provides collective knowledge, predictions, trending, reports, etc.

Bi-directional communication (wired or wireless) between ventilator 110 and the hosted knowledge portal can be accomplished via a WAN or LAN. For example, the wireless bi-directional communication can include 802.11/WiFi for communication with a LAN or a cellular modem for communication with a WAN.

In another embodiment, medical entity 120 is a hand held device. For example, the hand held device can be, but is not limited to, a tablet personal computer (PC), a personal digital assistant (PDA), a cell phone, a smart phone, etc. In such an embodiment, the wireless bi-directional communication can be accomplished via Bluetooth or other short range wireless communication protocols. As a result, in one embodiment, direct bi-directional communication can occur between ventilator 110 and the hand held device.

In various embodiments, communication 115, transmitted by ventilator 110, can include streaming ventilator data, a snapshot of ventilator data, etc. Additionally, communication 113, received by ventilator 110, can include remotely accessing/controlling ventilator 110, annotating ventilator data/information during rounds, etc.

In one embodiment, medical entity 120 is a medical device(s). For example, medical entity 120 is one or more of a ventilator, infuser, O2 sensor, patient orientation sensors, etc.

A wireless bi-directional communication between ventilator 110 and the bi-directional communication enabled medical device can include ZigBee or similar 802.15 devices for a wireless personal area network (WPAN). The communication system between the devices can be used for low rate networking.

Figure 2:
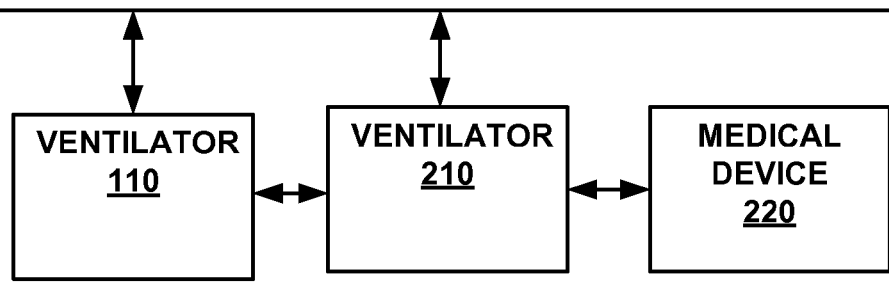
FIG. 2 illustrates an embodiment of a network of medical devices.

FIG. 2 depicts an embodiment of a network 200 of medical devices (e.g., ventilators, infusers, O2 sensors, patient orientation sensors, etc.) In particular, network 200 includes ventilators 110 and 210 and medical device 220. It should be understood that network 200 can include any number of a variety of medical devices.

In one embodiment, network 200 is an ad hoc wireless network of medical devices. For example, ventilator 110, 210 and medical device 220 are able to make daisy chain extensions within the range of a LAN or WAN when one WPAN enabled medical device or ventilator is within range of an access point (wired or wireless). In such an example, ventilator 210 utilizes ZigBee or similar 802.15 wireless protocol to connect to network 200 via an access point (not shown). As depicted, medical device 220, is not able to directly connect to the network because it is not within range of the access point. However, medical device 220 is within range of ventilator 210 and is able to wirelessly connect with ventilator 210. As such, ventilator 110, 210 and medical device 220 are able to make a daisy chain extensions within the range of a LAN or WAN.

Also, network 200 and associated devices are enabled for automated discovery of other enabled devices and auto setup of the WPAN.

Figure 3:
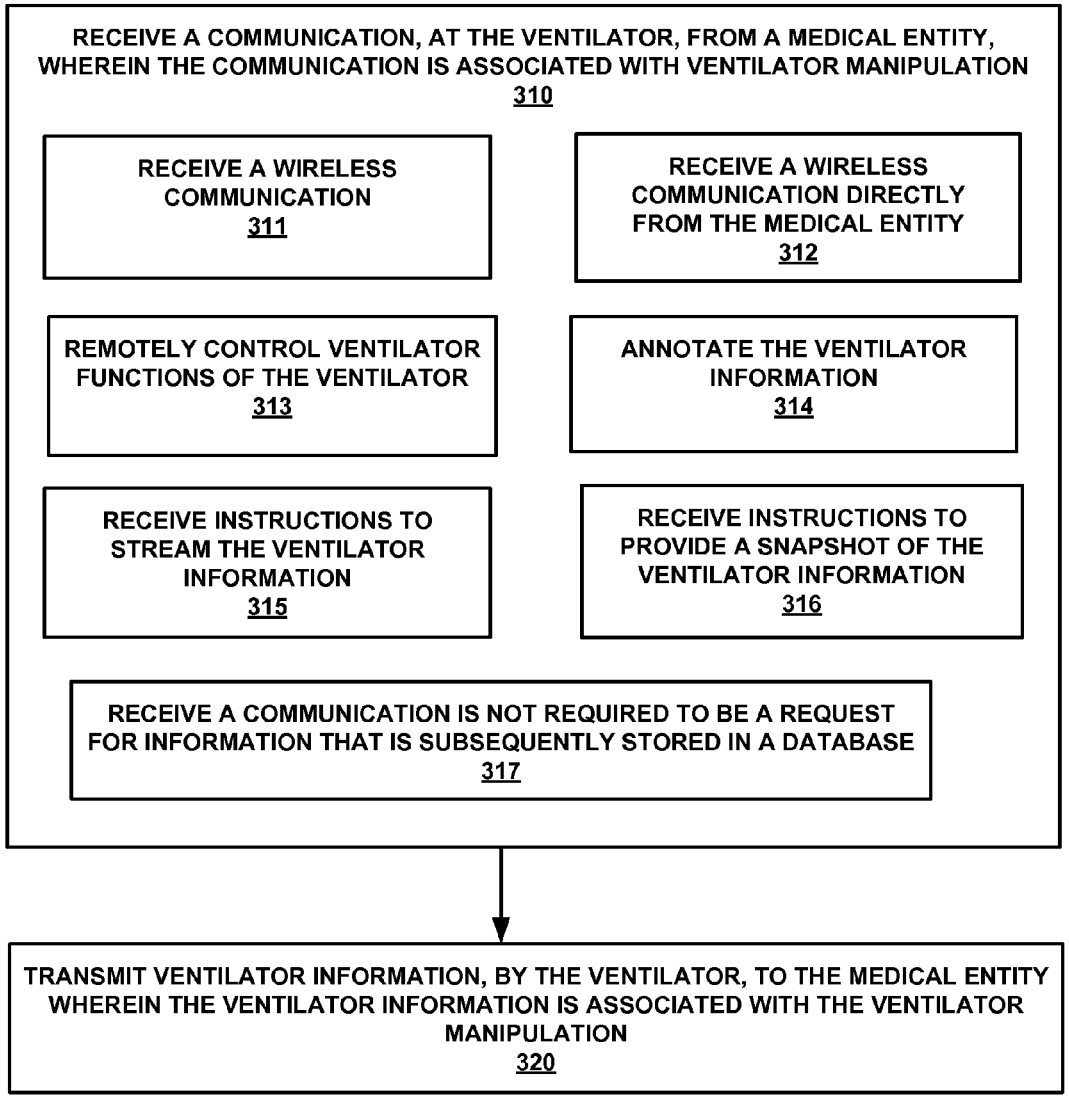
FIG. 3 illustrates an embodiment of a method for method for bi-directional ventilator communication.

FIG. 3 depicts an embodiment of a method 300 for method for bi-directional ventilator communication. In various embodiments, method 300 is carried out by processors and electrical components under the control of computer readable and computer executable instructions. The computer readable and computer executable instructions reside, for example, in a data storage medium such as computer usable volatile and non-volatile memory. However, the computer readable and computer executable instructions may reside in any type of computer readable storage medium. In some embodiments, method 300 is performed at least by system 100, as depicted in FIG. 1.

At 310 of method 300, a communication is received at the ventilator from a medical entity, wherein the communication is associated with ventilator manipulation. For example, ventilator 110 receives communication 113 from medical entity 120.

In one embodiment, at 311, a wireless communication is received. For example, ventilator 110 receives a wireless communication from medical entity 120.

In another embodiment, at 312, a wireless communication is received directly from the medical entity. For example, ventilator 110 receives a wireless communication directly from (e.g., without requiring any intermediary communication devices) a hand held device, such as, a smart phone.

In a further embodiment, at 313, the ventilator functions are remotely controlled. For example, ventilator functions (e.g., O2 levels, gas supply parameters, ventilator mode, etc.) of ventilator 110 are remotely controlled via medial entity 120.

In another embodiment, at 314, ventilator information is annotated. For example, a clinician annotates ventilator information of ventilator 110 in a rounding report via a tablet PC.

In one embodiment, at 315, instructions to stream ventilator information are received. For example, ventilator 110 receives instructions from medical entity 120 to stream ventilator information (e.g., communication 115) such that a clinician is able to view the ventilator information in real-time via a hand held device.

In another embodiment, at 316, instructions to provide a snapshot of the ventilator information are received. For example, ventilator 110 receives instructions from medical entity 120 to provide a snapshot of ventilator information such that a clinician is able to view the snapshot of the ventilator information at a hand held device.

In a further embodiment, at 317, a communication is received that is not required to be a request for information that is subsequently stored in a database. For example, communication 113 is not required to be a request for information that is subsequently stored in database. In such an example, communication 113 can be a request for information that is directly communicated from medical entity 120.

At 320, ventilator information is transmitted by the ventilator to the medical entity wherein the ventilator information is associated with the ventilator manipulation. For example, transmitter 114 transmits communication 115, wherein communication 115 is associated with information regarding the manipulation of ventilator functionality (e.g., confirmation of changed ventilator settings, etc.).

Contextualizing Ventilator Data

Figure 4:
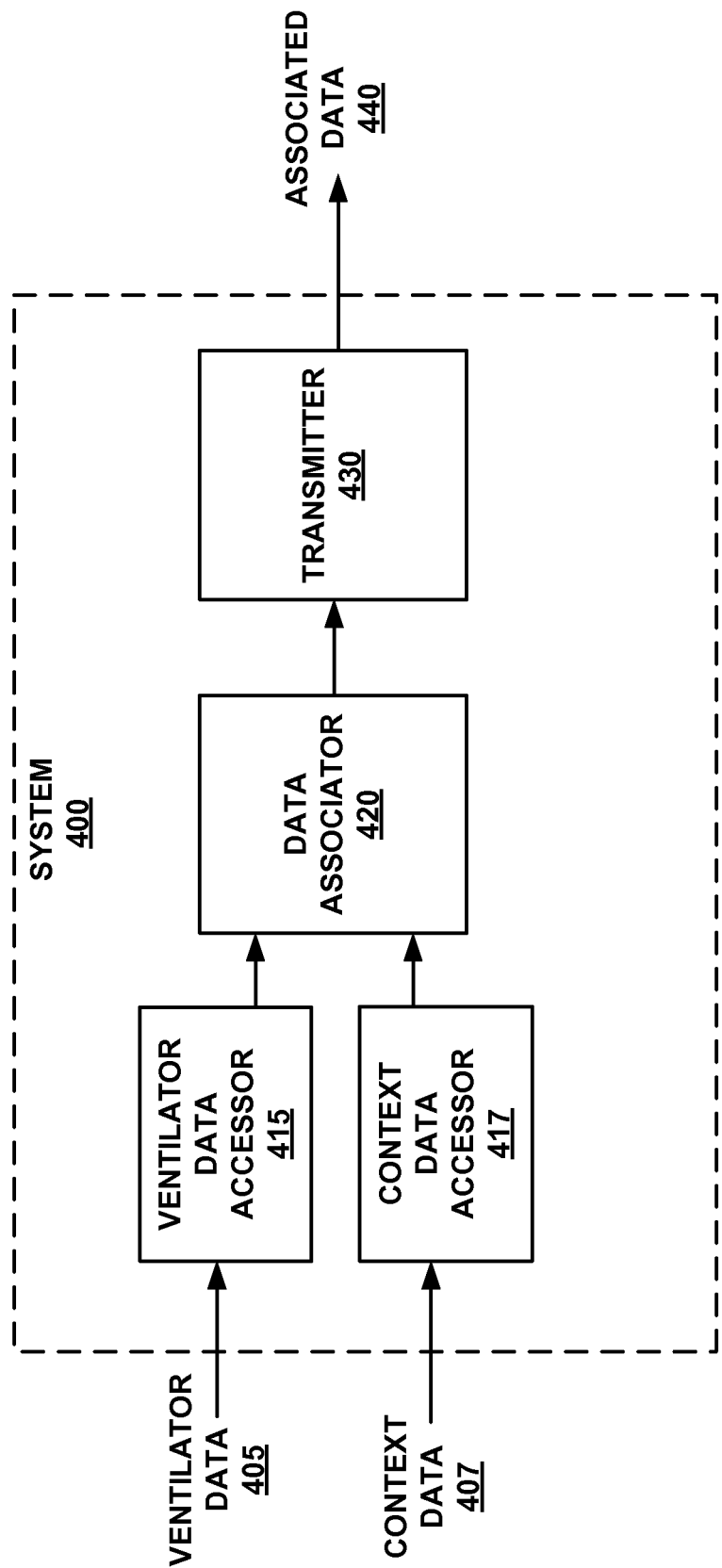
FIG. 4 illustrates an embodiment of a system for contextualizing ventilator data.

FIG. 4 depicts an embodiment of system 400 for contextualizing ventilator data. System 400 includes ventilator data accessor 415, context data accessor 417, data associator 420 and transmitter 430.

Ventilator data accessor 415 is for accessing ventilator data 405. Ventilator data 405 can be any information generated by the ventilator or information associated with ventilator functionality with regards to patient care. For example, ventilator data 405 can be, but is not limited to, ventilator mode, oxygen level, flow rates, timing, etc.

Context data accessor 417 is for accessing context data 407. Context data 407 can be any information that is able to provide context to ventilator data to enhance patient care via a ventilator. For example, context data 407 can be, but is not limited to, patient identification (ID), ventilator ID, caregiver ID, bed ID, location, etc.

In one embodiment, patient ID is associated with or issued from an Admit, Discharge, Transfer (ADT) system (not shown). As such, the patient ID allows system 400 to acquire additional patient specific information to be associated with ventilator data 405. The patient specific information can be, but not limited to, age, sex, height, weight, and treatment information associated with the patient, etc. It should be appreciated that treatment information can be, but is not limited to, surgery, acute care, burn recover, etc.

Patient ID can be accessed through patient logon with the ventilator. For example, a patient ID, which may be worn on a wrist of a patient, is scanned and the patient is subsequently logged on to the ventilator. As such, the patient ID is accessed.

Data associator 420 is configured for associating context data 407 and ventilator data 405 such that ventilator data 405 is contextualized. For example, ventilator data 405 is gas supply parameters and ventilator modes and context data 407 is the caregiver ID of the caregiver for the patient associated with the ventilator. Accordingly, data associator 420 associates the gas supply parameters and ventilator modes with the caregiver ID. Thus, the gas supply parameters and ventilator modes are contextualized by being associated with the caregiver ID.

In one embodiment, data associator 420 is further configured for associating a subset or a portion of ventilator data 405 with context data 407. For example, ventilator data 405 is associated with a caregiver ID and/or certain operations performed on the ventilator. In such an example, the caregiver ID may be accessed locally by scanning the caregiver ID (via a scanner coupled to the ventilator) or remotely (e.g., logon/password from the caregiver) such as through remote login or a hand held interface utilized by the caregiver. As a result, ventilator data 405 is associated with the caregiver (e.g., to a caregiver ID), which in turn, allows for forwarding of information to a hand held device or other device location.

In various embodiments, the caregiver ID is ascertained and/or verified for certain actions such as remote login, accessing certain stored/streaming data, changing certain ventilator settings, implementing an automated protocol, etc.

Transmitter 430 is configured to transmit associated data 440 that is generated by data associator 420. In one embodiment, transmitter 430 is configured to transmit associated data 440 to a hand held device of a caregiver.

In various embodiments, associated data 440 (or contextualized data) can be maintained on a ventilator or a server (e.g., a server application).

Figure 5:
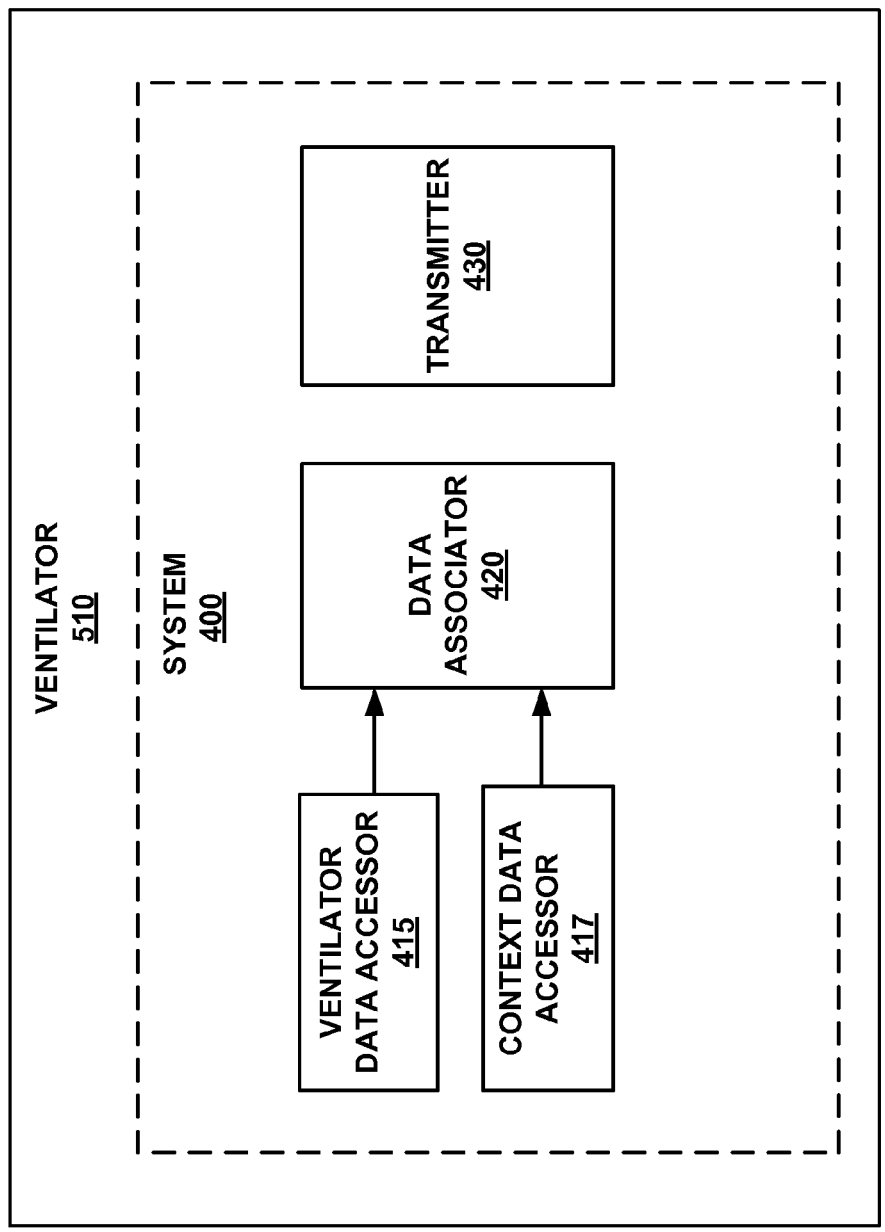
FIG. 5 illustrates an embodiment of a system for contextualizing ventilator data and a ventilator.

FIG. 5 depicts an embodiment of system 400 disposed in ventilator 510. In one embodiment, ventilator 510 is similar to ventilator 110. It should be understood that system 400 (or some of the components of system 400) may be disposed in another location separate from ventilator 510. For example, system 400 is disposed in a healthcare facility network or another medical device.

Figure 6:
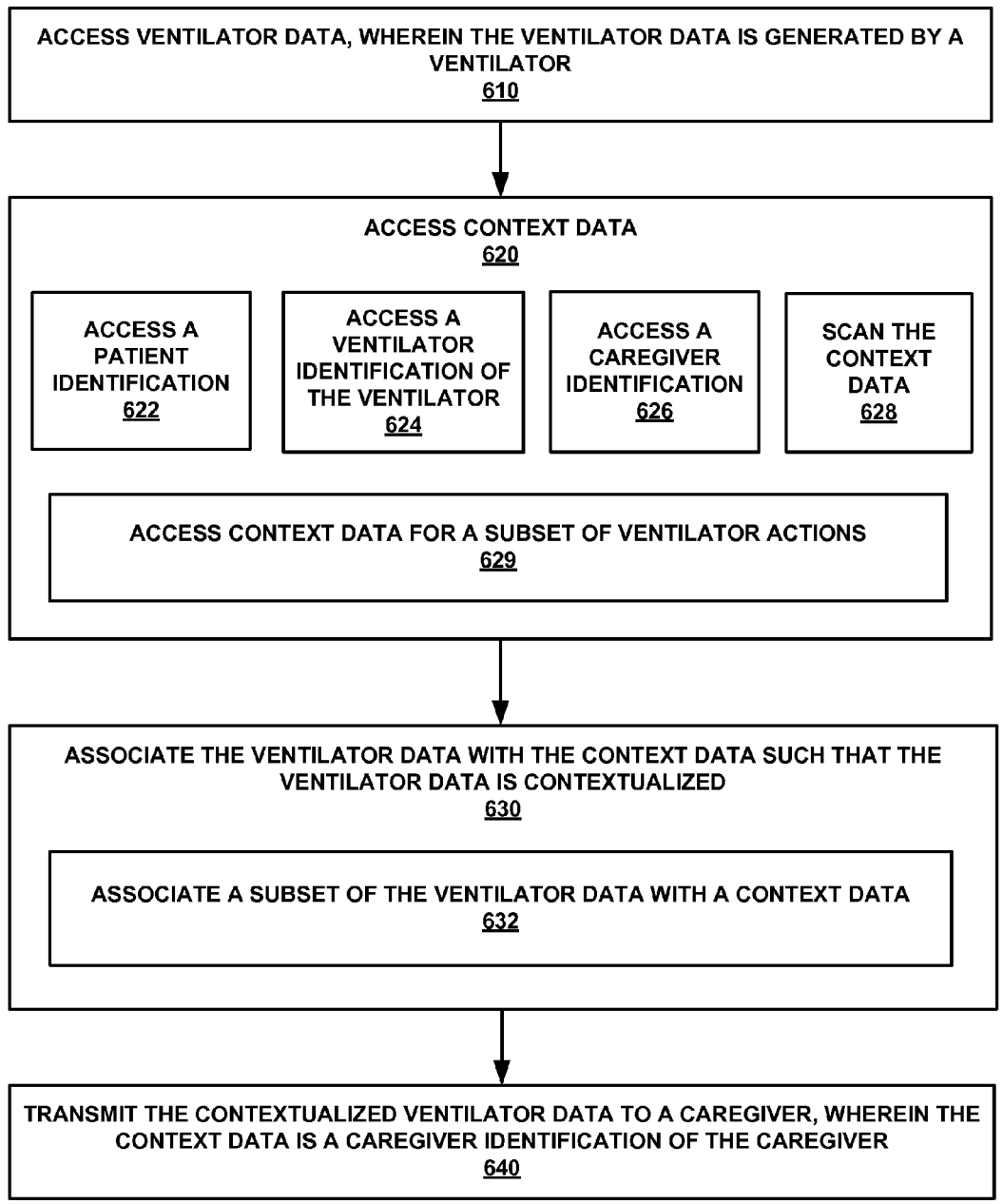
FIG. 6 illustrates an embodiment of a method for contextualizing ventilator data.

FIG. 6 depicts an embodiment of a method 600 for contextualizing ventilator data. In various embodiments, method 600 is carried out by processors and electrical components under the control of computer readable and computer executable instructions. The computer readable and computer executable instructions reside, for example, in a data storage medium such as computer usable volatile and non-volatile memory. However, the computer readable and computer executable instructions may reside in any type of computer readable storage medium. In some embodiments, method 600 is performed at least by system 400, as depicted in FIG. 4.

At 610 of method 600, ventilator data is accessed, wherein the ventilator data is generated by a ventilator. For example, ventilator data 405 is accessed by ventilator data accessor 415, wherein ventilator data 405 is generated by ventilator 510.

At 620, context data is accessed. For example, context data 407 is accessed by context data accessor 417.

In one embodiment, at 622, a patient ID is accessed. For example, a patient wristband is scanned to access a patient ID or any other unique patient information (e.g., age, sex, height, weight, etc.).

In another embodiment, at 624, a ventilator ID is accessed. For example, a ventilator ID of ventilator 510 is accessed for contextualizing ventilator data 405.

In a further embodiment, at 626, a caregiver ID is accessed. For instance, a caregiver ID (or any other unique caregiver information) is accessed to facilitate in contextualizing ventilator data 405. As a result, associated data 440 is able to be transmitted to a hand held device utilized by the caregiver.

In another embodiment, at 628, context data is scanned. For example, a caregiver ID is scanned in order to access the caregiver ID. In another example, context data is scanned via auto ID technology (e.g., bar codes, RFID, fingerprint, etc.).

In one embodiment, at 629, context data is accessed for a subset of ventilator actions. For example, a caregiver ID is accessed/verified for certain ventilator actions, such as remote login, storing/streaming data, change certain ventilator settings, etc.

At 630, associate the ventilator data with the context data such that the ventilator data is contextualized. For instance, data associator 420 associates ventilator data 405 and context data 407 to generate associated data 440, such that ventilator data 405 is contextualized.

In one embodiment, at 632, a subset of the ventilator data is associated with the context data. For example, ventilator data 405 is gas supply parameters and ventilator modes for an entire duration that a patient is associated with the ventilator. Context data 407 is a first caregiver ID of a plurality of caregivers for the patient associated with the ventilator. Accordingly, data associator 420 associates the gas supply parameters and ventilator modes with the first caregiver ID (rather than a second and third caregiver ID for a second and third caregiver for the patient). Thus, a portion or subset of ventilator data 405 is associated with the first caregiver ID.

At 640, the contextualized ventilator data is transmitted to a caregiver, wherein the context data is a caregiver identification of the caregiver. For example, associated data 440 is transmitted to a tablet PC of the caregiver who is responsible for the care of the patient.

Ventilator Component Module

Figure 7:
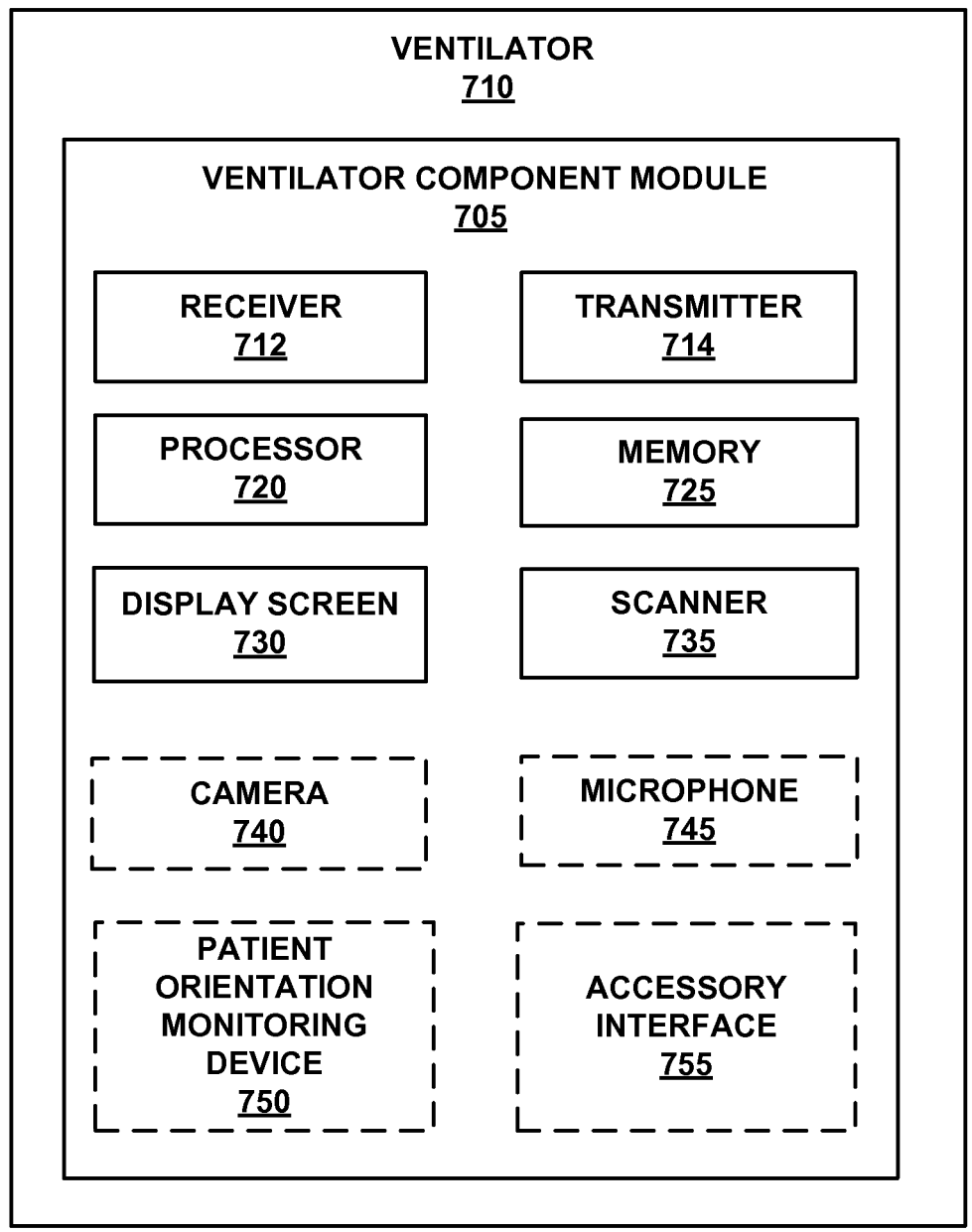
FIGS. 7 and 8 illustrate embodiments of a ventilator and ventilator component module.

FIG. 7 depicts ventilator 710. In one embodiment, ventilator 710 is similar to ventilator 110, however, ventilator 710 includes ventilator component module 705.

Ventilator component module 705 is configured for housing a plurality of ventilator components that are utilized by ventilator 710 to enhance the functionality of ventilator 710. Ventilator component module 705 includes receiver 712, transmitter 714, processor 720, memory 725, display screen 730, scanner 735 and optionally camera 740, microphone 745, patient orientations monitoring device 750, and an accessory interface 755. It should be understood that ventilator component module 705 can include other devices/components that are utilized by ventilator 710 to enhance the functionality of ventilator 710.

Receiver 712 and transmitter 714 are similar to receiver 112 and transmitter 114, respectively, as described above.

Processor 720 can be any processor that is configured for processing data, applications, and the like for ventilator 710.

Memory 725 is for storing ventilator information. For example, memory 725 stores ventilator data 405, context data 407 and/or associated data 440.

Display screen 730 is for displaying ventilator information. For example, display screen 730 displays a ventilator mode, patient ID, clinician ID, etc. In one embodiment, display screen 730 is a touch display screen that allows access to data on other networked ventilators and/or medical devices.

Scanner 735 is any information reader (e.g., bar code reader, RF reader, etc.) that is able to read medical information that is utilized by ventilator 710. For example, scanner 735 is able to scan patient IDs, caregiver IDs, ventilator IDs, etc.

Camera 740 is for providing image capture functionality for ventilator 710. For example, camera 740 may capture images of a patient, caregiver, other medical devices to facilitate in the care or security of a patient associated with ventilator 710.

Microphone 745 is for providing audio capture functionality for ventilator 710. For example, microphone 745 may capture audio data of a patient to facilitate in the care of a patient associated with ventilator 710.

Patient orientation monitoring device 750 is for monitoring the orientation of a patient associated with ventilator 710. For example, patient orientation monitoring device 750 monitors whether the patient is on his/her side, back stomach, etc.

Accessory interface 755 (wired or wireless) is configured to interface other components/devices with ventilator 710. For example, accessory interface 755 is a Universal Serial Bus (USB) interface for third party accessories (e.g., a video camera).

It should be understood that ventilator 710 is operable and provides basic ventilator functionality to provide care for a patient, without ventilator component module 705. However, ventilator component module 705 and its respective components enhance the functionality of ventilator 710, as described above.

Figure 8:
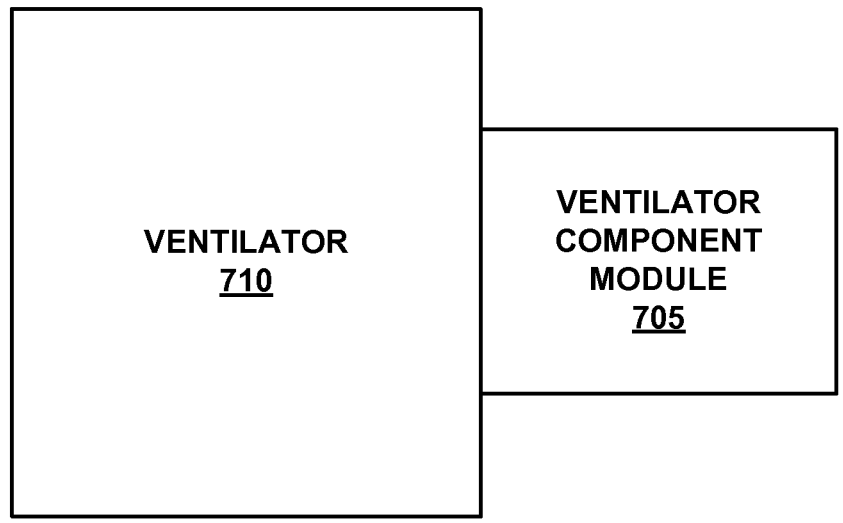

Ventilator component module 705 is disposed within the housing of ventilator 710 or is integral with the housing of ventilator 710. However, ventilator component module 705 may also be releasably attached to ventilator 710, as depicted in FIG. 8. This allows for upgrades to ventilator 710. For example, a version of ventilator component module 705 may easily be swapped out with a new version of ventilator component module 705. Additionally, the releasably attached ventilator component module also facilitates in managing regulatory compliance in the event that some components/functions of the ventilator component module are not immediately approved for patient use.

Automatic Implementation of a Ventilator Protocol

Figure 9:
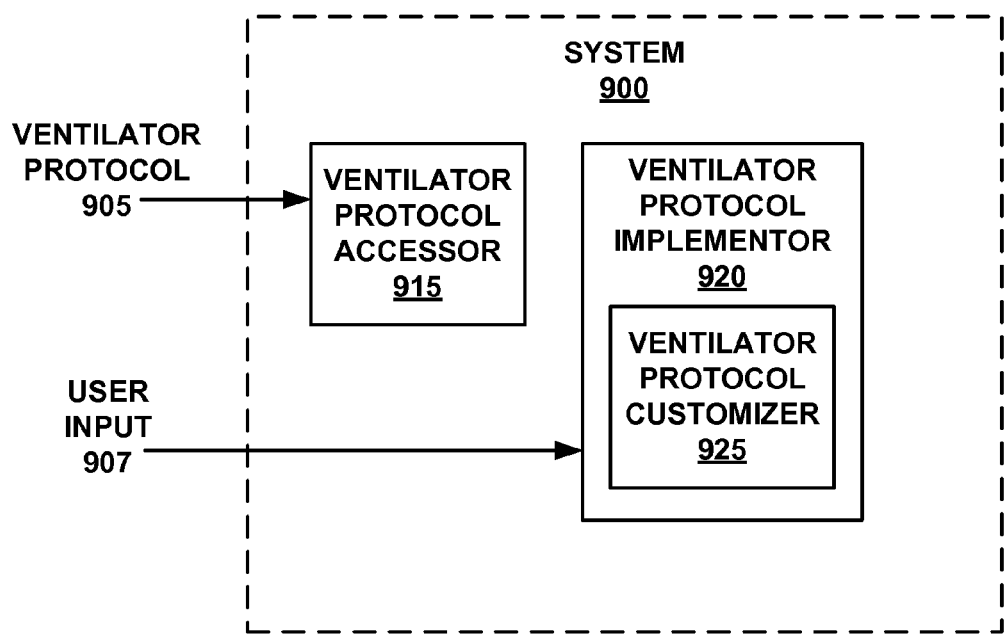
FIG. 9 illustrates an embodiment of a system for automatically implementing a ventilator protocol.

FIG. 9 depicts an embodiment of system 900 for automatically implementing a ventilator protocol. System 900 includes ventilator protocol accessor 915, ventilator protocol implementor 920, and ventilator protocol customizer 925. System 900 can be disposed in a ventilator, for example, ventilator 710, as described in detail above. System 900 can be implemented in a location separate from ventilator, for example, in a healthcare facility network.

Ventilator protocol accessor 915 is for accessing ventilator protocol 905. Ventilator protocol 905 can be any protocol facilitating in the control of ventilator functionality. For example, ventilator protocol 905 can pertain to oxygen level, flow rate, timing, etc. In various embodiments, ventilator protocol 905 can be, but is not limited to, a weaning protocol, an acute care protocol, a neonatal O2 protocol, and a lung protection protocol. In one embodiment, a protocol can be described as a decision tree with respect to ventilator control and functionality. In another embodiment, ventilator protocol 905 provides instructions to clinicians on what to do with respect to the ventilator.

Ventilator protocol 905 may be native to a ventilator and thus, provided by a ventilator (e.g., ventilator 710). In other embodiments, ventilator protocol 905 may be pushed/accessed from other systems, such as, but not limited to, a hosted (or deployed) knowledge portal or a hospital healthcare system.

Ventilator protocol implementor 920 is configured for implementing ventilator protocol 905 via a touch screen display of a ventilator (e.g., display screen 730). In other words, ventilator protocol implementor 920 is configured to implement protocol 905 on a ventilator by way of user input 907 at the ventilator. For example, one or more ventilator protocols (e.g., weaning protocol, lung protection protocol, etc.) may be displayed on a touch display screen of a ventilator. A caregiver then selects (via the touch display screen) which ventilator protocol is to be implemented on the ventilator for patient care. Accordingly, based on user input 907, ventilator protocol implementor 920 automatically implements the selected ventilator protocol on the ventilator.

In various embodiments, ventilator protocol 905 is implemented in combination with a medical device, such as an infusion pump.

Also, ventilator protocol 905 can be controlled or implemented (to some extent) based on patient input. For example, a conscious patient may be able to increase/reduce ventilatory support by self-selection within a protocol-defined range.

Ventilator protocol customizer 925 is configured for customizing ventilator protocol 905. Ventilator protocol customizer 925 can customize ventilator protocol 905 based on unique patient information, for example, a patient ID, patient lab results, patient test results, etc. It should be appreciated that the patient information can be accessed from an ADT system.

Figure 10:
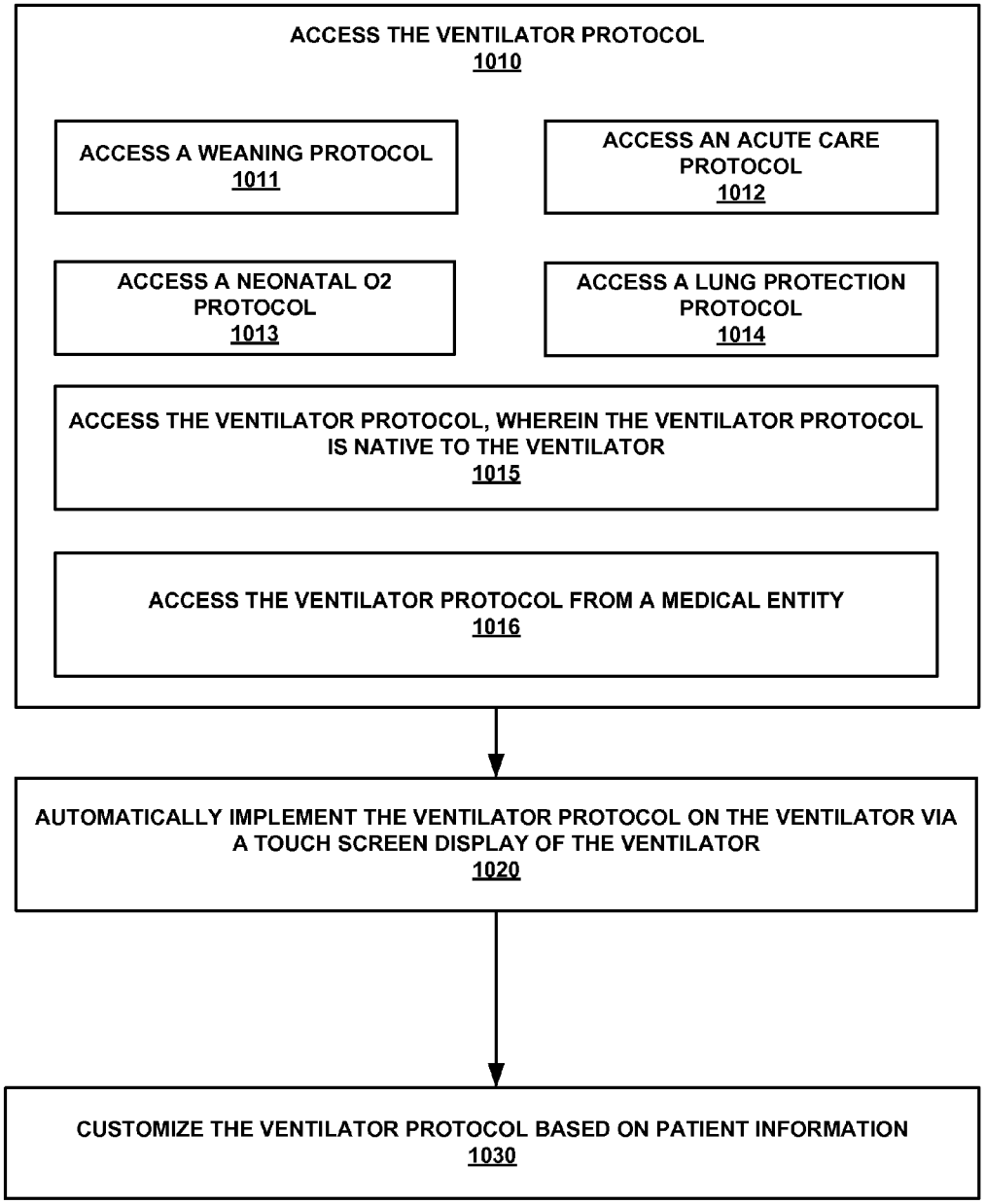
FIG. 10 illustrates an embodiment of a method for automatically implementing a ventilator protocol.

FIG. 10 depicts an embodiment of a method 1000 for implementing a ventilator protocol. In various embodiments, method 1000 is carried out by processors and electrical components under the control of computer readable and computer executable instructions. The computer readable and computer executable instructions reside, for example, in a data storage medium such as computer usable volatile and non-volatile memory. However, the computer readable and computer executable instructions may reside in any type of computer readable storage medium. In some embodiments, method 1000 is performed at least by system 900, as depicted in FIG. 9.

At 1010 of method 1000, a ventilator protocol is accessed. For instance, ventilator protocol 905 is accessed by ventilator protocol accessor 915.

In one embodiment, at 1011, a weaning protocol is accessed. In another embodiment, at 1012, an acute care protocol is accessed. In a further embodiment, at 1013, a neonatal O2 protocol is accessed. In yet another embodiment, a lung protection protocol is accessed.

In one embodiment, at 1015, the ventilator protocol is accessed, wherein the ventilator protocol is native to the ventilator. For example, ventilator protocol 905 is accessed, wherein ventilator protocol 905 is native to ventilator 710.

In a further embodiment, at 1016, the ventilator protocol is accessed from a medical entity. For example, ventilator protocol 905 is accessed from medical entity 120.

At 1020, the ventilator protocol on the ventilator is automatically implemented via a touch screen display of the ventilator. For example, a caregiver selects a protocol displayed on a display screen. Accordingly, ventilator protocol implementor 920 automatically implements the selected protocol on the ventilator.

At 1030, the ventilator protocol is customized based on patient information. For example, ventilator protocol customizer 925 customizes ventilator protocol based on patient lab results.

Implementing Ventilator Rules on a Ventilator

Figure 11:
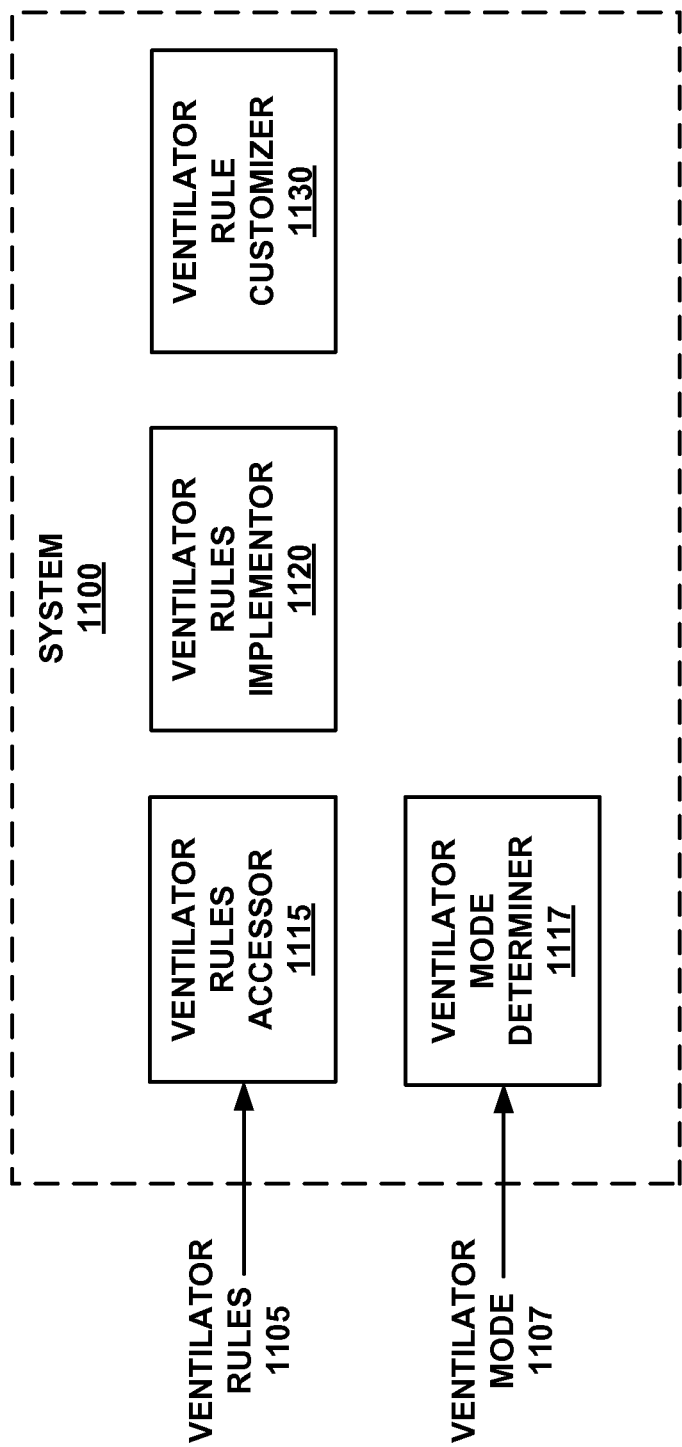
FIG. 11 illustrates an embodiment of a system for implementing a ventilator rule on a ventilator.

FIG. 11 depicts an embodiment of system 1100 for implementing a ventilator rule on a ventilator. System 1100 includes ventilator rule accessor 1115, ventilator mode determiner 1117, ventilator rules implementor 1120, and ventilator rules customizer 1130. System 1100 can be disposed in a ventilator, for example, ventilator 710. System 1100 can be implemented in a location separate from ventilator, for example, in a healthcare facility network.

Ventilator rules accessor 1115 is configured for accessing ventilator rules 1105 for a ventilator. Ventilator rules 1105 can be any rule that affects the functionality of a ventilator. For example, ventilator rules 1105 can be, but are not limited to, ventilator function control and gas supply parameters, such as, gas flow rates, etc.

In one embodiment, ventilator rules 1105 can be subset of a protocol. For example, if a certain protocol is implemented then particular rules associated with that specific protocol can be utilized.

In another embodiment, ventilator rules 1105 are not associated or part of a protocol. For example, the rule that a warning appears when a battery is dead is not associated with a protocol.

In one embodiment, ventilator rules 1105 are native to a ventilator (e.g., ventilator 710), thus, ventilator rules 1105 are provided by the ventilator. In another embodiment, ventilator rules 1105 are accessed from a location, other than the ventilator, for example, from a healthcare facility network (for local rules) or from a knowledge portal (for best practice rules).

Ventilator mode determiner 1117 is configured to determine which mode(s) the ventilator is operating in. For example, a ventilator mode can be, but is not limited to, a pediatric ventilation mode. Depending on the determined ventilator mode of operation, a variety of rules can be displayed on a display screen of the ventilator and/or certain features can be disabled to prevent patient harm, which will be described in further detail below.

Ventilator rules implementor 1120 is configured for implementing at least one of the ventilator rules 1105 in response to a determined mode of operation. For example, if the ventilator is in a pediatric ventilation mode, certain rules pertaining to gas supply may be implemented.

In one embodiment, if a certain rule is implemented, then certain ventilator functions may be locked out, for example, certain gas supply parameters may be locked out to prevent patient harm.

Also, if a certain rule is desired to be implemented, then a specific override may be required to in order to implement the desired rule. This would prevent unintentionally interrupting the implementation of the rule. For example, if a ventilator is running in accordance to a first rule, and a second rule is intended to be implemented which conflicts with the first rule, then an override of the second rule may be required.

Ventilator rule customizer 1130 is configured to customize ventilator rules 1105. In one embodiment, ventilator rules 1105 are customized based on patient contextualized data (e.g., age, sex, weight). For example, maximum and minimum fresh gas flow may be customized based on age, sex or weight of a patient. Customization can take place within the ventilator or may be pushed to the ventilator from an outside device/location.

Figure 12:
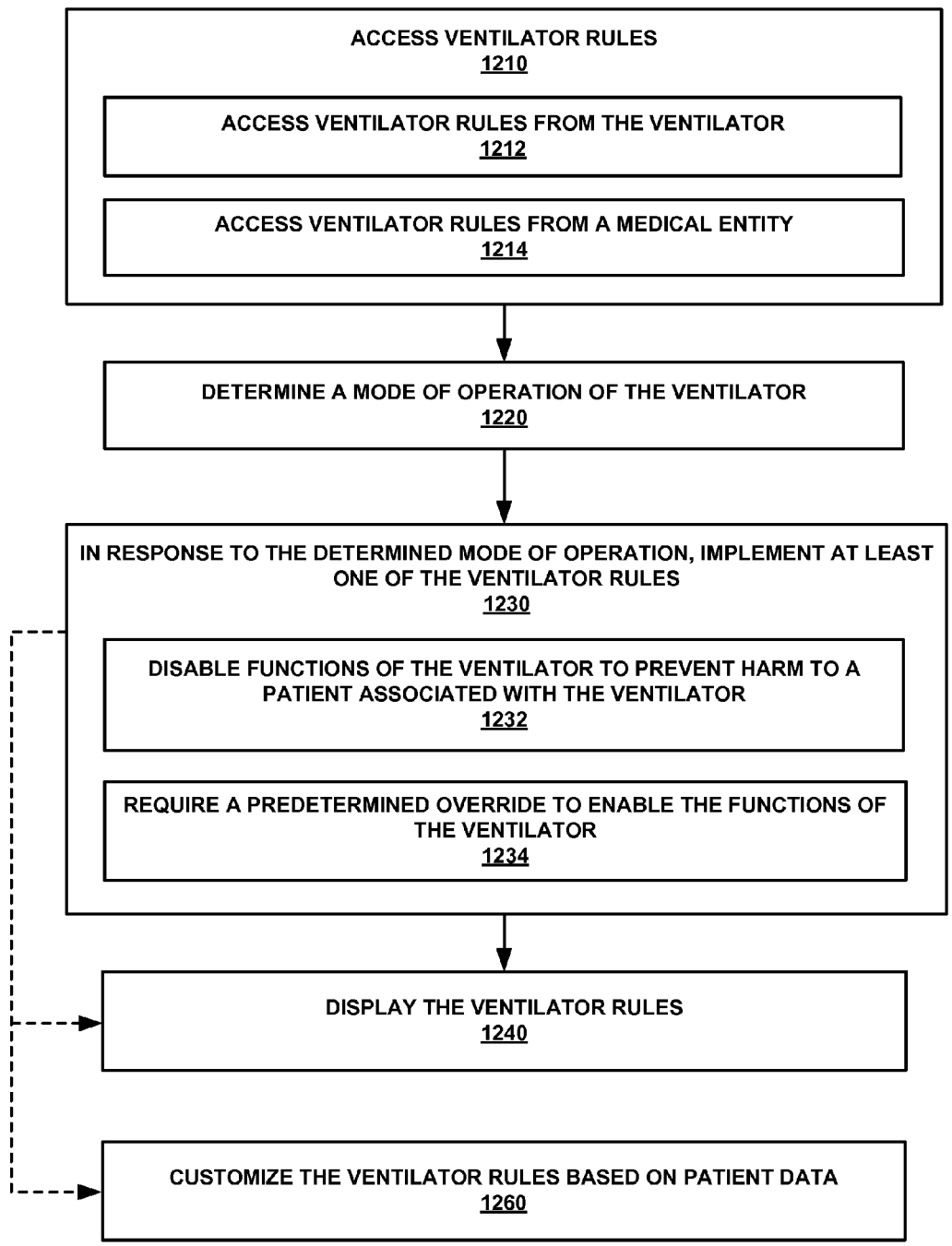
FIG. 12 illustrates an embodiment of a method for implementing a ventilator rule on a ventilator.

FIG. 12 depicts an embodiment of a method 1200 for implementing a ventilator protocol. In various embodiments, method 1200 is carried out by processors and electrical components under the control of computer readable and computer executable instructions. The computer readable and computer executable instructions reside, for example, in a data storage medium such as computer usable volatile and non-volatile memory. However, the computer readable and computer executable instructions may reside in any type of computer readable storage medium. In some embodiments, method 1200 is performed at least by system 1100, as depicted in FIG. 11.

At 1210 of method 1200, ventilator rules are accessed. For example, ventilator rules accessor 1115 accesses a plurality of rules that affect gas flow rates, ventilator function control, etc.

In one embodiment, at 1212, ventilator rules are accessed from a ventilator. For example, ventilator rules 1105 are accessed from ventilator 710. In another embodiment, at 1214, ventilator rules are accessed from a medical entity, such as a ventilator knowledge portal.

At 1220, a mode of operation of the ventilator is determined. For example, ventilator mode determiner 1117 determines that ventilator mode 1107 is a neonatal ventilator mode.

At 1230, in response to the determined mode of operation, at least one of the ventilator rules implemented. For example, ventilator rules implementor 1120 implements a particular max/min flow rate in response to a neonatal ventilation mode.

In one embodiment, at 1232, ventilator functions are disabled to prevent harm to a patient associated with the ventilator. For example, certain gas supply functions are disabled to prevent patient harm, in response to a determined mode of operation.

In another embodiment, at 1234, a predetermined override is required to enable the functions of the ventilator. For example, if a ventilator function is disabled, then a predetermined override is required to enable the disabled functions of the ventilator.

At 1240, the ventilator rules are displayed. For example, ventilator rules 1105 are displayed on a display screen.

At 1250, ventilator rules are customized based on patient data. For example, ventilator rule customizer 1130 customizes ventilator rules 1105 based on patient age, sex, height, etc.

Healthcare Facility Ventilation Management

Figure 13:
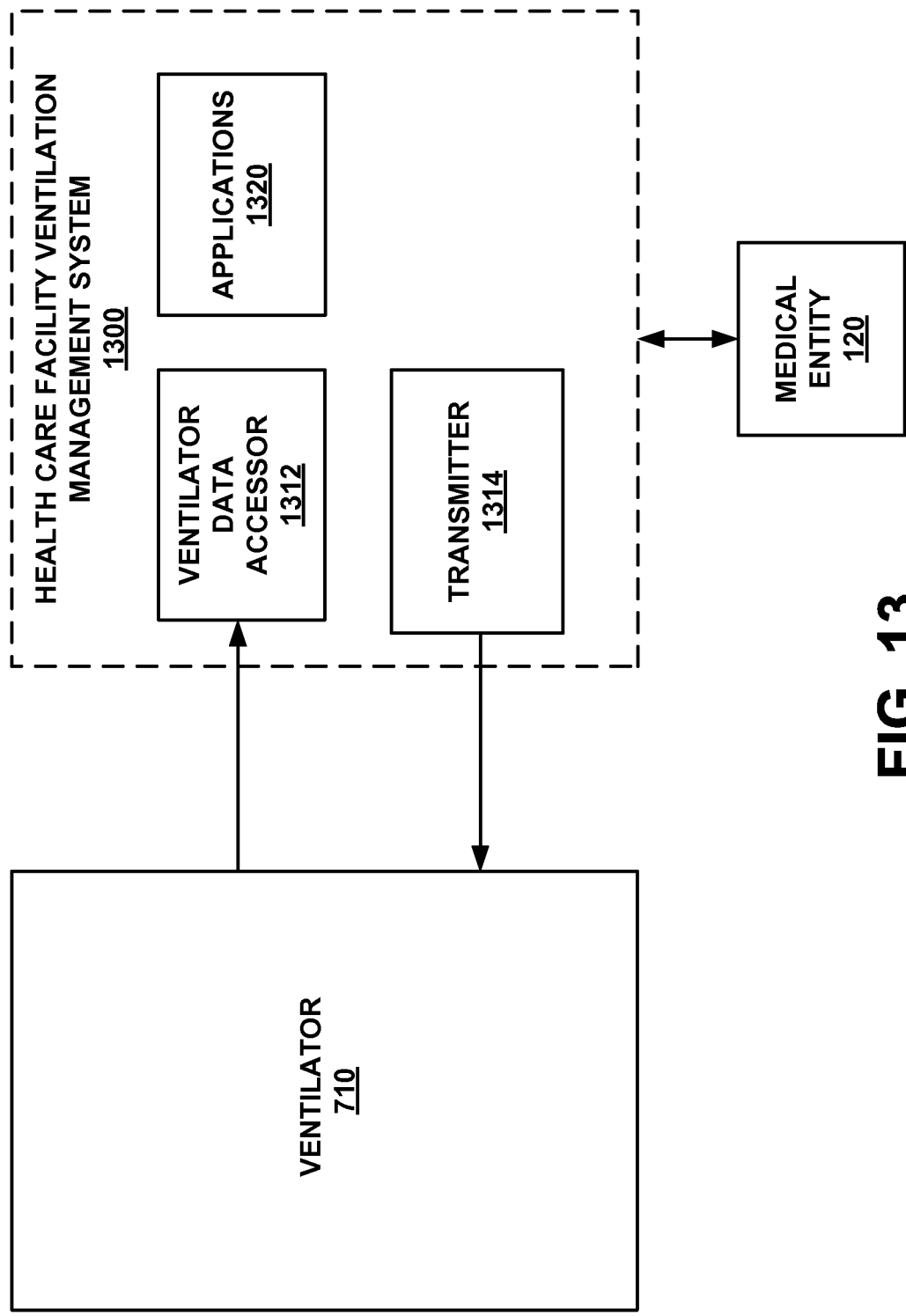
FIG. 13 illustrates an embodiment of a healthcare facility ventilation management system.

FIG. 13 depicts an embodiment of healthcare facility ventilation management system 1300. System 1300 is associated with a healthcare facility network and is configured to bi-directionally communicate with one or more ventilators (e.g., 710) and/or one or more medical entities (e.g., medical entity 120). The bi-directional communication of system 1300 is similar to the bi-directional communication as described above. In various embodiments, the bi-directional communication is wired or wireless (e.g., 802.11 WiFi) bi-directional communication. In one embodiment, system 1300 is implemented (or runs on) ventilator 710.

In particular, system 1300 includes ventilator data accessor 1312, transmitter 1314 and applications 1320.

Ventilator data accessor 1312 is for accessing ventilator data from ventilator 710 (or any other ventilators and/or medical devices). For example, data (e.g., logged in ventilator or streamed from ventilator) is remotely accessed.

Transmitter 1314 is for transmitting a communication/data to a ventilator and/or a medical entity, which will be described in further detail below. In one embodiment, transmitter 1314 transmits ADT information to a ventilator.

Applications 1320 are any application that is utilized by system 1300 for ventilation management. For example, applications 1320 (or other systems described herein), can be, but are not limited to, a billing application, an inventory control application, cost avoidance application, remote access application, harm avoidance application, protocol application and a rules customization application. It is understood that applications 1320 are related to the variety of systems described herein. As such, system 1300 includes and/or utilizes a plurality of systems and functions described herein.

In one embodiment, system 1300 includes and utilizes batch data management. For example, batches of data are able to be sent from a ventilator without real-time communication.

In one embodiment, system 1300 utilizes system 400 for contextualizing ventilator data, which is described in detail above. In such an example, data associator 420 associates context data 407 and ventilator data 405 such that ventilator data 405 is contextualized. Additionally, transmitter 1314 transmits the contextualized data to medical entity 120 (e.g., hand held device, ventilator knowledge portal, etc.).

In another embodiment, system 1300 utilizes system 900 for automatically implementing a ventilator protocol, as described in detail above. For example, ventilator protocol implementor 902 implements a protocol on a ventilator by way of user input at the ventilator.

Furthermore, ventilator protocol customizer 925 customizes ventilator a protocol based on unique patient information, for example, a patient ID, patient lab results, patient test results, etc. It should be understood that the protocols are pushed to the ventilator from system 1300, for example, by transmitter 1314.

In a further embodiment, system 1300 utilizes system 1100 for implementing a ventilator rule on a ventilator, as described in detail above. For example, ventilator rules implementor 1120 implements at least one of the ventilator rules 1105 in response to a determined mode of operation. In such an example, if the ventilator is in a pediatric ventilation mode, certain rules pertaining to gas supply may be implemented.

Furthermore, ventilator rules 1105 are customized based on patient contextualized data (e.g., age, sex, weight). For example, maximum and minimum fresh gas flow may be customized based on age, sex or weight of a patient. It should be understood that the rules are pushed to the ventilator from system 1300, for example, by transmitter 1314.

It should be appreciated that rules and protocols an result in the ventilator doing something automatically (e.g., closed loop) or can result in user guidance (e.g., open loop).

Figure 14:
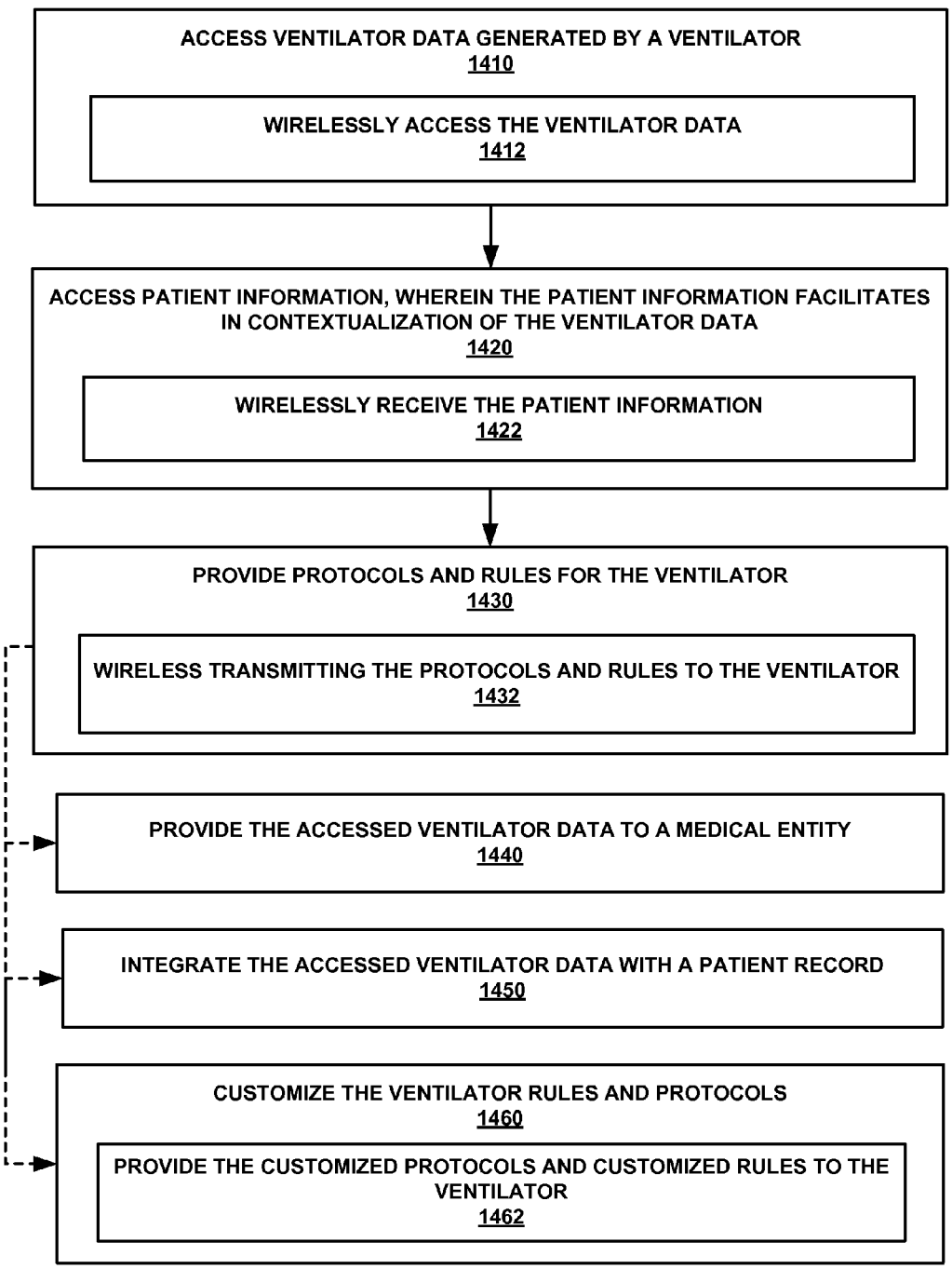
FIG. 14 illustrates an embodiment of a method for healthcare facility ventilation management.

FIG. 14 depicts an embodiment of a method 1400 for healthcare facility ventilation management. In various embodiments, method 1400 is carried out by processors and electrical components under the control of computer readable and computer executable instructions. The computer readable and computer executable instructions reside, for example, in a data storage medium such as computer usable volatile and non-volatile memory. However, the computer readable and computer executable instructions may reside in any type of computer readable storage medium. In some embodiments, method 1400 is performed at least by system 1300, as depicted in FIG. 13.

At 1410 of method 1400, ventilator data generated by a ventilator is accessed. For example, ventilator data accessor 1312 accesses ventilator data from ventilator 710.

In one embodiment, at 1412, the ventilator data is wirelessly accessed. For example, ventilator data accessor 1312 wirelessly accesses ventilator data from ventilator 710 via 802.11 WiFi.

At 1420, patient information is accessed, wherein the patient information facilitates in contextualization of the ventilator data. For example, context data (e.g., age, sex, height, etc.) is accessed.

In one embodiment, at 1422, the patient information is wirelessly received. For example, context information is wirelessly received from a medical entity (e.g., medical entity 120).

At 1430, protocols and rules are provided for the ventilator. For example, ventilator protocol implementor 902 implements a protocol on a ventilator by way of user input at the ventilator and ventilator rules implementor 1120 implements at least one of the ventilator rules 1105 in response to a determined mode of operation. In one embodiment, the protocols and rules are wirelessly transmitted to the transmitter.

At 1440, accessed ventilator data is provided to a medical entity. For example, transmitter 1314 transmits the ventilator data to a hand held device.

At 1450, the accessed ventilator data is integrated with a patient record. For example, ventilator data is integrated with unique patient information such that the ventilator data is contextualized.

At 1460, the ventilator rules and protocols are customized. For example, ventilator rule customizer 1130 customizes ventilator rules 1105 based on patient lab results, medications prescribed, etc. In one embodiment, at 1462, the customized protocols and rules are provided to the ventilator (e.g., ventilator 710).

Wide Area Ventilation Management

Figure 15:
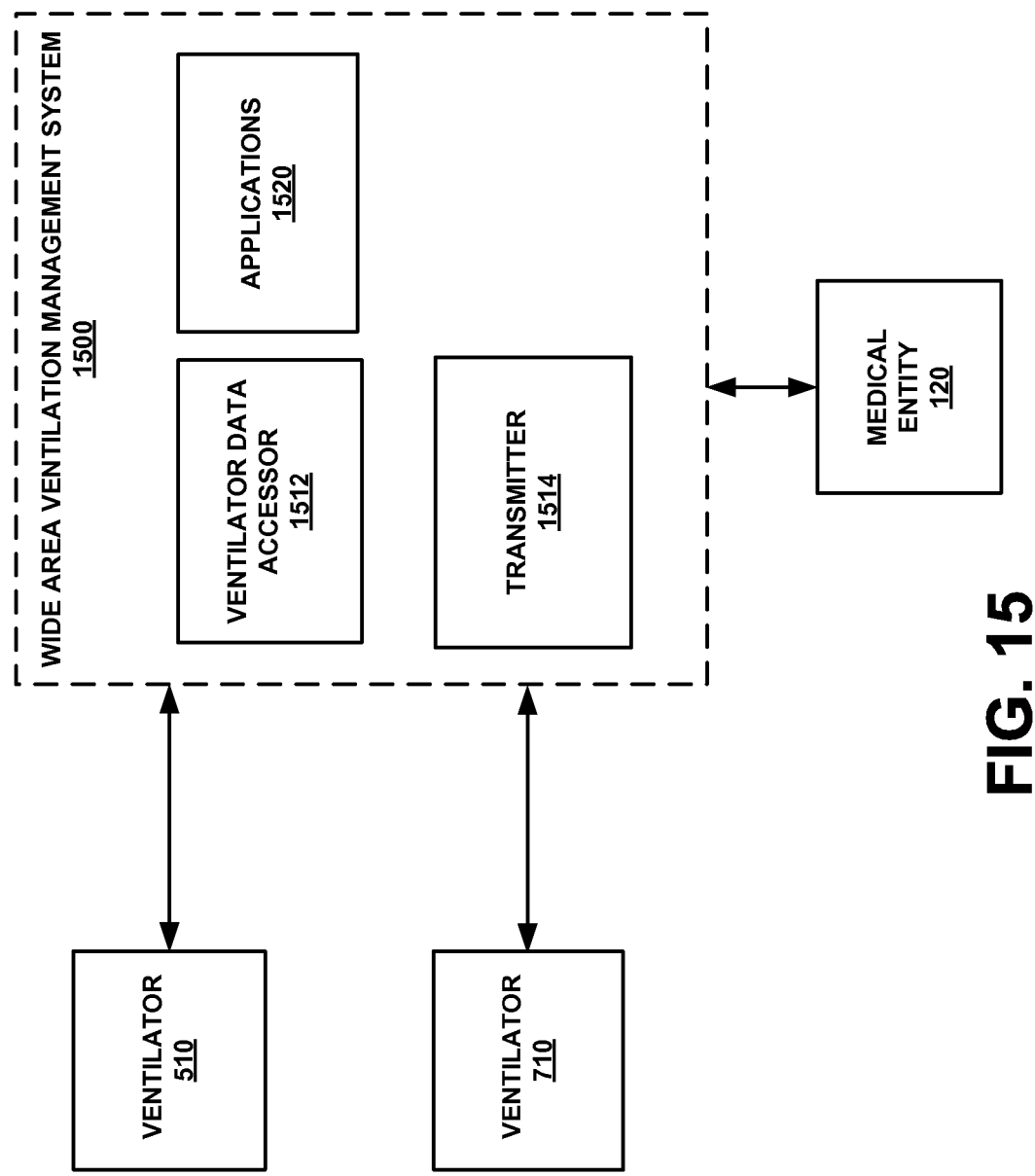
FIG. 15 illustrates an embodiment of a wide area ventilation management system.

FIG. 15 depicts an embodiment of wide area ventilation management system 1500. System 1500 is associated with a wide area network and is configured to bi-directionally communicate with one or more ventilators (e.g., 710) and/or one or more medical entities (e.g., medical entity 120). The bi-directional communication of system 1500 is similar to the bi-directional communication as described above. In one embodiment, wireless bi-directional communication is provided via a cellular network.

In particular, system 1500 includes ventilator data accessor 1512, transmitter 1514 and applications 1520.

Ventilator data accessor 1512 is for accessing ventilator data from ventilators 510 and/or 710 (or any other ventilators and/or medical devices). For example, data (e.g., logged in ventilator or streamed from ventilator) is remotely accessed.

Transmitter 1514 is for transmitting a communication/data to ventilators and/or a medical entity, which will be described in further detail below. In one embodiment, transmitter 1514 transmits ADT information (or other data) to a ventilator. In various embodiments, transmitter 1514 transmits data to a healthcare facility network to facilitate monitoring patient outcomes after they have been discharged. Additionally, data may be transmitted (or received) in a particular Electronic Medication Administration Record (eMAR) format (e.g., level 7 compatible interface).

Applications 1520 are any application that is utilized by system 1500 for ventilation management. For example, applications 1520 (or other systems described herein), can be, but are not limited to, a billing application, an inventory control application, cost avoidance application, remote access application, harm avoidance application, protocol application and a rules customization application. It is understood that applications 1520 are related to the variety of systems described herein. As such, system 1500 includes and/or utilizes a plurality of systems and functions described herein.

In one embodiment, system 1500 utilizes system 400 for contextualizing ventilator data, which is described in detail above. In such an example, data associator 420 associates context data 407 and ventilator data 405 such that ventilator data 405 is contextualized. Additionally, transmitter 1514 transmits the contextualized data to medical entity 120 (e.g., hand held device, ventilator knowledge portal, etc.).

In another embodiment, system 1500 utilizes system 900 for automatically implementing a ventilator protocol, as described in detail above. For example, ventilator protocol implementor 902 implements a protocol on a ventilator by way of user input at the ventilator.

Furthermore, ventilator protocol customizer 925 customizes a ventilator protocol based on unique patient information, for example, a patient ID, patient lab results, patient test results, etc. It should be understood that the protocols are pushed to the ventilator from system 1500, for example, by transmitter 1514.

In a further embodiment, system 1500 utilizes system 1100 for implementing a ventilator rule on a ventilator, as described in detail above. For example, ventilator rules implementor 1120 implements at least one of the ventilator rules 1105 in response to a determined mode of operation. In such an example, if the ventilator is in a pediatric ventilation mode, certain rules pertaining to gas supply may be implemented.

Furthermore, ventilator rules 1105 are customized based on patient contextualized data (e.g., age, sex, weight). For example, maximum and minimum fresh gas flow may be customized based on age, sex or weight of a patient. It should be understood that the rules are pushed to the ventilator from system 1500, for example, by transmitter 1514.

Figure 16:
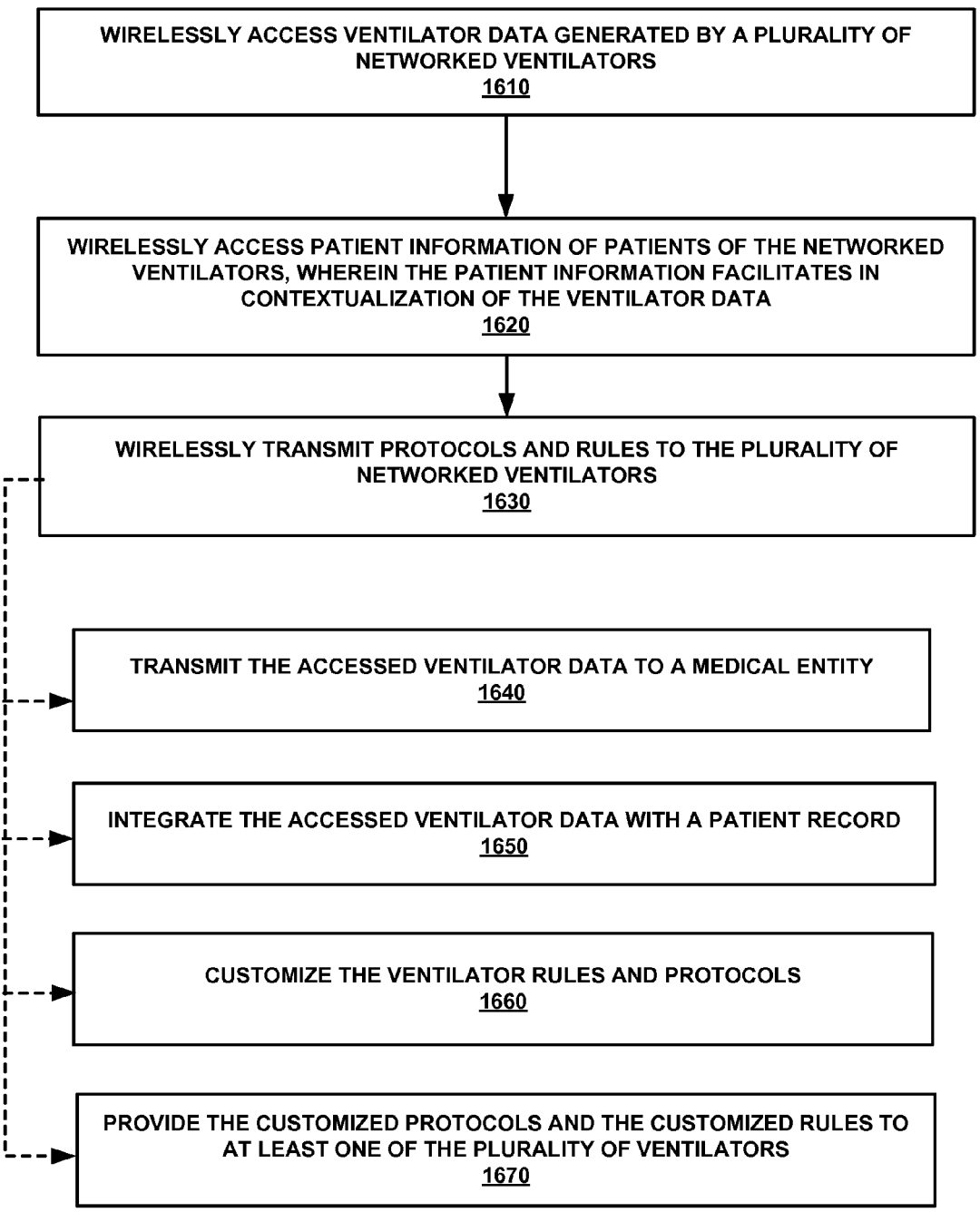
FIG. 16 illustrates an embodiment of a method for wide area ventilation management.

FIG. 16 depicts an embodiment of a method 1600 for wide area ventilation management. In various embodiments, method 1600 is carried out by processors and electrical components under the control of computer readable and computer executable instructions. The computer readable and computer executable instructions reside, for example, in a data storage medium such as computer usable volatile and non-volatile memory. However, the computer readable and computer executable instructions may reside in any type of computer readable storage medium. In some embodiments, method 1600 is performed at least by system 1500, as depicted in FIG. 15.

At 1610, ventilator data generated by a plurality of networked ventilators is accessed. For example, ventilator data generated by ventilators 510 and 710 is wirelessly accessed via a WAN.

At 1620, wirelessly access patient information of patients of the networked ventilators is wirelessly accessed, wherein the patient information facilitates in contextualization of the ventilator data. For example, patient information of patients associated with ventilators 510 and 710 is wirelessly accessed, wherein the patient information facilitates in contextualization of the ventilator data, as described above.

At 1630, protocols and rules are wirelessly transmitted to the plurality of networked ventilators. For example, protocols and rules are wirelessly transmitted to ventilator 510 and 710.

At 1640, the accessed ventilator data is transmitted to a medical entity. For example, the ventilator data is transmitted to medical entity 120 (e.g., a hand held device associated with a caregiver).

At 1650, the accessed ventilator data is integrated with a patient record. For example, the accessed ventilator data is associated with unique patient data such that the ventilator data is contextualized.

At 1660, the ventilator rules and protocols are customized. For example, the rules are customized based on a ventilator mode and the protocols are customized based on patient information.

At 1670, the customized protocols and the customized rules are provided to at least one of the plurality of ventilators. For example, the customized rules and protocols are wirelessly transmitted to at least one of the ventilators (e.g., ventilator 710).

Analyzing Medical Device Data

Figure 17:
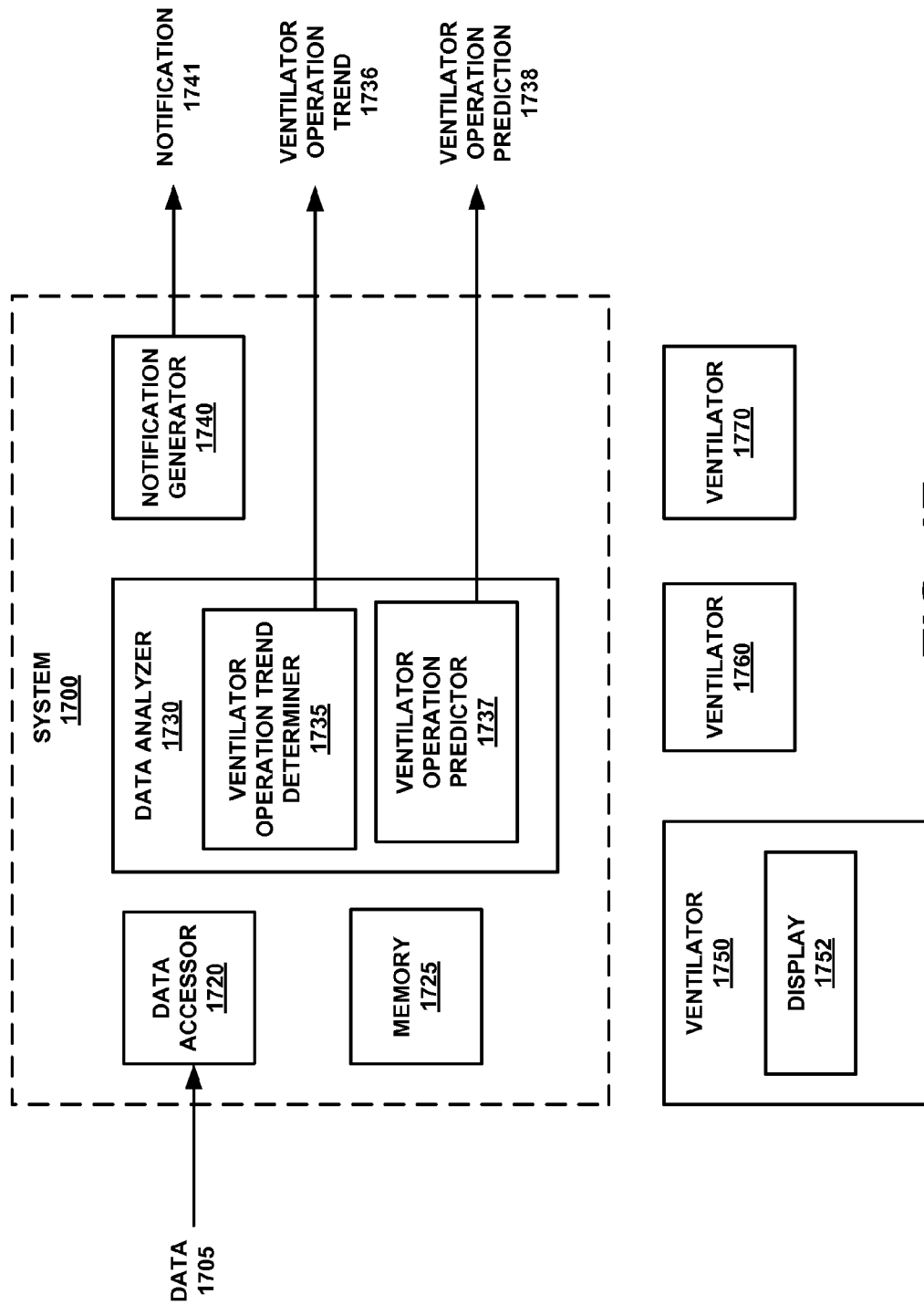
FIGS. 17, 19, 21, 23, 25, 27 and 29 illustrate embodiments of a medical system.

FIG. 17 depicts an embodiment of system 1700. System 1700 can be described as a ventilation knowledge portal. As will be described in detail below, system 1700 or ventilation knowledge portal provides information which may assist a clinician or caregiver in observing and inputting certain information with respect to a ventilator. In one embodiment, system 1700 is an embodiment of medical entity 120.

In general, system 1700 is configured for analyzing medical device data, such as data associated with a ventilator(s). Moreover, the analysis (e.g., based on clinical data analysis, disease management strategies, etc.) of medical device data provides continuous quality improvement (CQI) analysis and reporting for ventilators, giving a hospital/caregiver ability to make improvements.

System 1700 includes data accessor 1720, data analyzer 1730 and notification generator 1740. Moreover, system 1700 includes ventilators 1750-1770. Although FIG. 17 depicts three ventilators, it should be appreciated that system 1700 includes at least one ventilator.

Data accessor 1720 is configured for accessing data from a plurality of ventilators. For instance, data accessor 1720 accesses data 1705 from ventilators 1750-1770. In various embodiments, data accessor 1720 can access data from a single ventilator or any number of ventilators (e.g., ventilators 110, 510 and/or 710).

Data 1705 can be any information, provided by a ventilator, such as, information that facilitates in assisting a clinician in observing and inputting certain information for patient care. Data 1705 can be, but is not limited to, modes of operation, vent settings, patient vital signs, breath sounds, patient orientation, etc.

Data analyzer 1730 is configured for analyzing an aggregate of data 1705. Data analyzer 1730 includes ventilator operation trend determiner 1735 and ventilator operation predictor 1737.

Ventilator operation trend determiner 1735 is configured for determining an operational trend 1736 for a ventilator(s), such as ventilators 1750-1770, based on data 1705.

Ventilator operation predictor 1737 is configured for predicting a ventilator operation prediction 1738 for ventilator(s), such as ventilators 1750-1770, based on data 1705.

Notification generator 1740 is configured for generating notification 1741 for one or more ventilators.

System 1700 can be connected to a variety of networks, such as but not limited to, healthcare facility networks, wide area networks, etc. Additionally, system 1700 can also be coupled directly to ventilators, such as ventilators 1750-1770. In one embodiment, one or more components of system 1700 are located within a ventilator.

During use of system 1700, ventilators 1750-1770 are in operation with respective patients. During operation of ventilators 1750-1770, ventilators 1750-1770 generate data 1705 which is accessed by data accessor 1720. Data 1705 is the aggregate data from ventilators 1750-1770. However, if only one ventilator is in operation or connected to system 1700, then data 1705 is data only from that single ventilator.

The ventilators are capable of bi-directional communication with system 1700. That is, the ventilators are able to send information to system 1700 and also receive information from system 1700. In various embodiments, the ventilators can include a camera, information scanner, touch screen display, microphone, memory, etc.

It should be appreciated that data 1705 is accessed over any time period. For example, data 1705 can be the aggregate data provided over days or months. In one embodiment, data 1705 can be stored in memory 1725.

Data analyzer 1730 receives data 1705. In general, data analyzer 1730 facilitates in analyzing data 1705 to provide information which may assist a clinician in observing and inputting certain information with respect to a ventilator.

Ventilator operation trend determiner 1735 determines ventilator operation trend 1736 based on data 1705. In general, ventilator operation trend 1736 applies to a general tendency or course of a particular ventilator's operation with a particular patient based on data 1705.

Ventilator operation predictor 1737 determines ventilator operation prediction 1738 based on ventilator operation trend 1736 and/or data 1705. In general, ventilator operation prediction 1738 applies to an operation of a particular ventilator with a particular patient.

Ventilator operation prediction 1738 can be based on specific ventilator modes of operation and/or patient vitals that are compared to aggregated data 1705. Accordingly, this allows a clinician to know that certain outcomes are likely. Thus, the clinician can prepare accordingly, or provide proactive treatment to prevent the outcomes.

In various embodiments, ventilator operation trend 1736 and/or ventilator operation prediction 1738 provides information that assists a clinician in observing and inputting certain information related to, but not limited to: delivery of neonatal oxygen, lung protective strategy, sedation effects or events surrounding sedation, weaning effects, suction effects, and transpulmonary pressure, etc. Also, ventilator operation trend 1736 and/or ventilator operation prediction 1738 can be displayed on a ventilator's screen, hand-held device, or other network device.

Notification generator 1740 generates notification 1741 based on ventilator operation trend 1736 and/or aggregated data 1705. In other words, system 1700 monitors certain modes of operation and/or patient vitals. Accordingly, notification 1741 is generated for notifying a clinician of various levels of modes of operation and/or patient vitals.

Notification 1741 can be customized. For example, notification 1741 can be selected to be a warning tone in response to: negative trend analysis, ventilation being performed which contradicts with an assigned protocol, or violation of a rule, etc. In various embodiments, notification 1741 is sent to a nursing station, supervisor, care giver, pager, etc.

Figure 18:
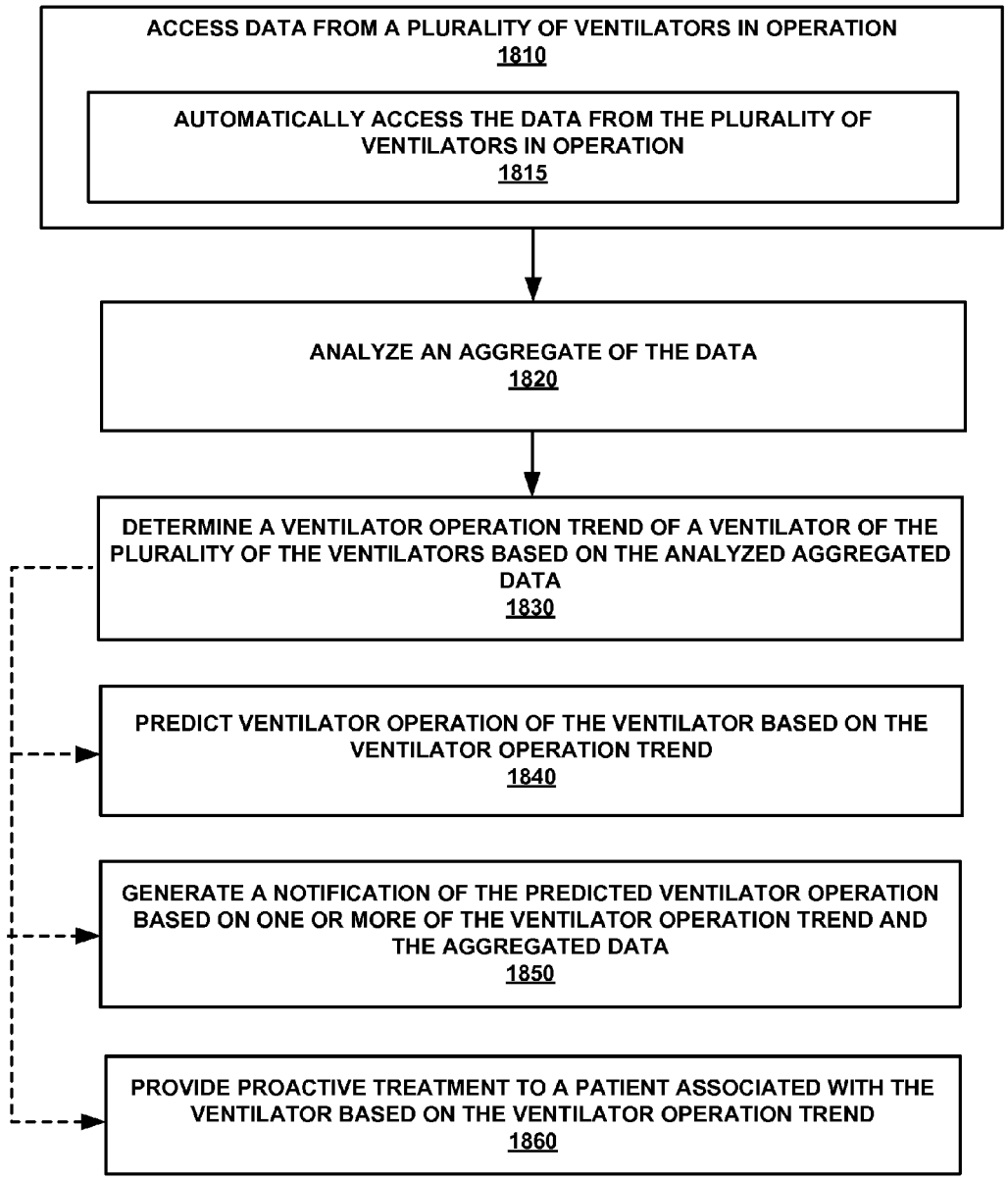
FIG. 18 illustrates an embodiment a method for analyzing medical device data.

FIG. 18 depicts an embodiment of a method 1800 for analyzing medical device data. In various embodiments, method 1800 is carried out by processors and electrical components under the control of computer readable and computer executable instructions. The computer readable and computer executable instructions reside, for example, in a data storage medium such as computer usable volatile and non-volatile memory. However, the computer readable and computer executable instructions may reside in any type of computer readable storage medium. In some embodiments, method 1800 is performed at least by system 1700, as depicted in FIG. 17.

At 1810 of method 1800, data is accessed from a plurality of ventilators in operation. For example, data 1705 is aggregated data from ventilators 1750-1770 and is accessed by data accessor 1720. In one embodiment, at 1815, data 1705 is automatically accessed from ventilators 150-170.

At 1820, an aggregate of the data is analyzed. For example, data analyzer 1730 (or other components) analyzes data 1705.

At 1830, a ventilator operation trend of a ventilator is determined based on the analyzed aggregated data. For example, ventilator operation trend determiner 1735 determines ventilator operation trend 1736 based on analyzed data 1705.

At 1840, a ventilator operation of the ventilator is predicted based on the ventilator operation trend. For example, ventilator operation predictor 1737 predicts ventilator operation prediction 1738 based on ventilator operation trend 1736.

At 1850, a notification of the predicted ventilator operation is predicted based on one or more of the ventilator operation trend and the aggregated data. For example, notification generator 1740 generates notification 1741 of predicted ventilator operation based on ventilator operation trend 1736 and/or data 1705.

At 1860, a proactive treatment is provided to a patient associated with the ventilator based on the ventilator operation trend.

Ventilator Report Generation

Figure 19:
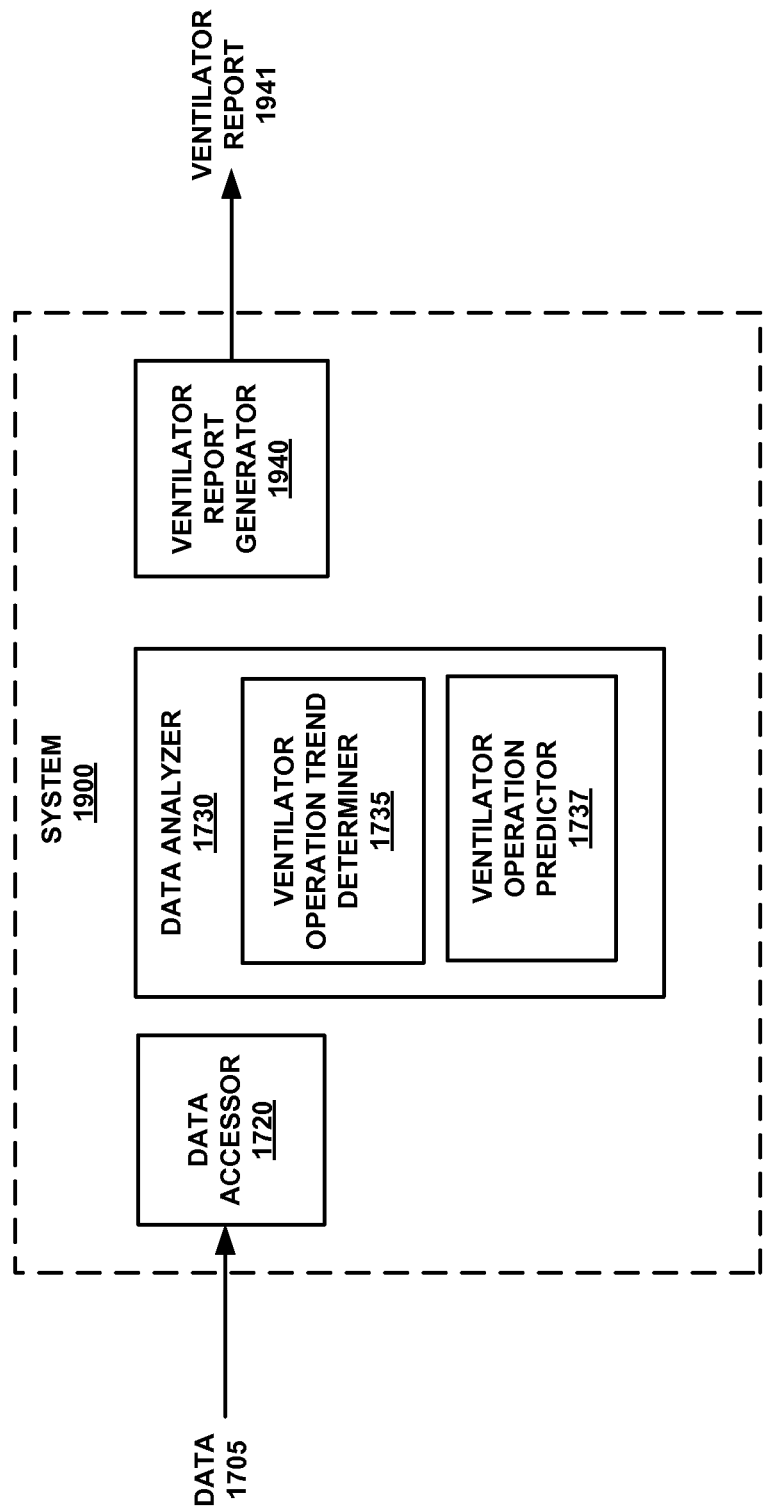

FIG. 19 depicts an embodiment of system 1900 for ventilation report generation. It should be appreciated that system 1900 is similar to system 1700, however, system 1900 includes ventilator report generator 1940 configured for generating report 1941. Ventilator report generator 1940 generates ventilator report 1941 for a ventilator based on the analyzed aggregated data.

Ventilator report 1941 can be a variety of different reports. In one embodiment, ventilator report 1941 is a protocol compliance (or success analysis) report which compares the success of a ventilator protocol to other similar protocols. In such a report, the report is based on aggregated data of a plurality of ventilators (e.g., ventilators 1750-1770).

In another embodiment, ventilator report 1941 is a rounding report. Typically, a rounding report is for a clinician or caregiver and summarizes key information from a shift. As such, the rounding report allows for streamlined changeover at the end of a shift of one caregiver and the beginning of a shift of another caregiver. The rounding report can be generated as a service.

In various embodiments, ventilator report 1941 can be based on trend analysis or comparison to aggregated ventilator information. For example, a report can compare best practice rules and/or protocols to collected data to determine discrepancies. Accordingly, the discrepancies are a part of the report.

Figure 20:
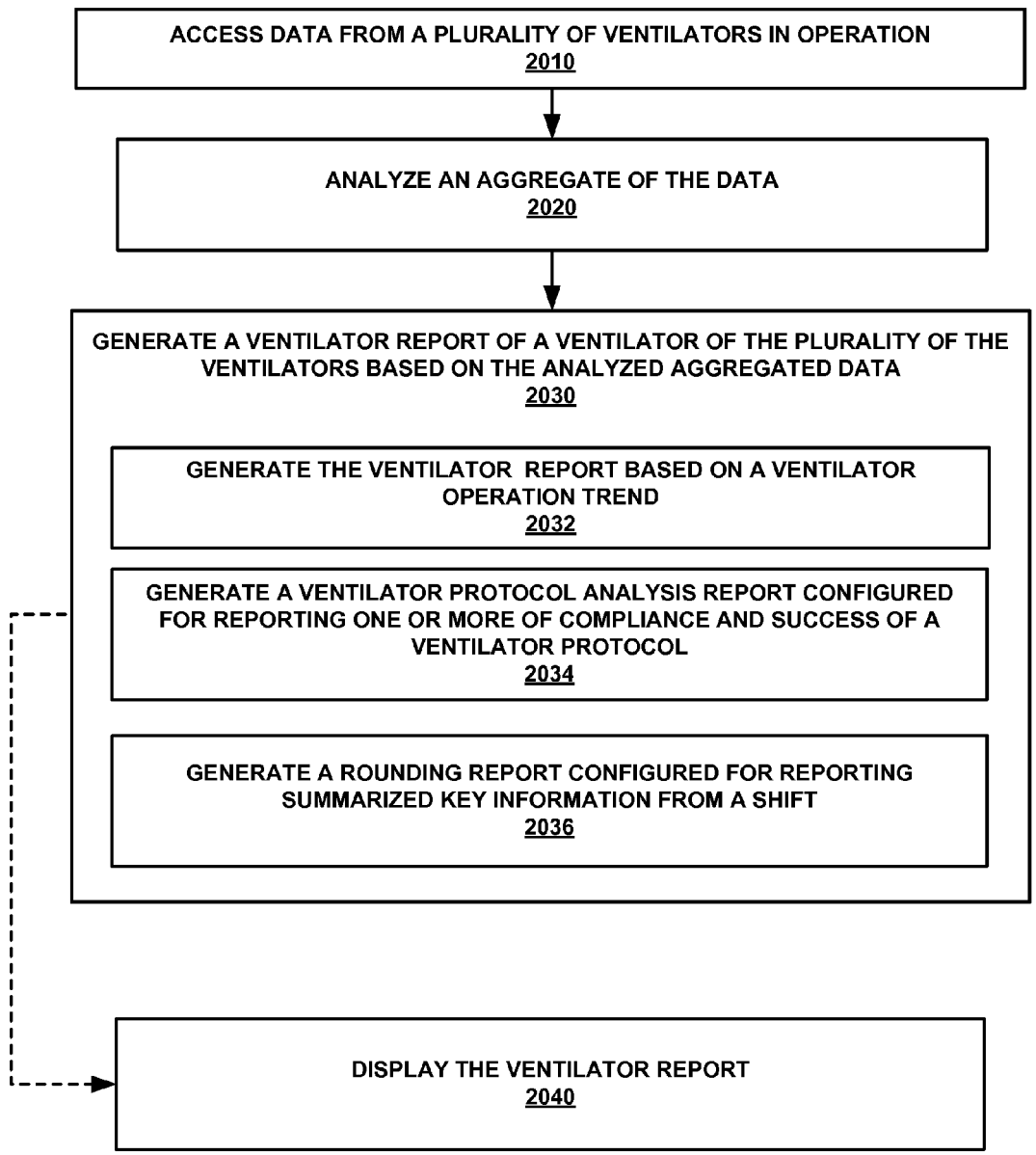
FIG. 20 illustrates an embodiment a method for generating a ventilator report.

FIG. 20 depicts an embodiment of a method 2000 for generating a ventilator report. In various embodiments, method 2000 is carried out by processors and electrical components under the control of computer readable and computer executable instructions. The computer readable and computer executable instructions reside, for example, in a data storage medium such as computer usable volatile and non-volatile memory. However, the computer readable and computer executable instructions may reside in any type of computer readable storage medium. In some embodiments, method 2000 is performed at least by system 1900, as depicted in FIG. 19.

At 2010 of method 2000, data is accessed from a plurality of ventilators in operation. At 2020, an aggregate of the data is analyzed.

At 2030, a ventilator report of a ventilator is generated based on the analyzed aggregated data. For example, ventilator report generator 1940 generates ventilator report 1941 based on data 1705.

In one embodiment, at 2032, the ventilator report based on a ventilator operation trend. For example, ventilator report generator 1940 generates ventilator report 1941 based on ventilator operation trend 1736.

In another embodiment, at 2034, a ventilator protocol analysis report is generated and configured for reporting one or more of compliance and success of a ventilator protocol.

In a further embodiment, at 2036, a rounding report is generated and configured for reporting summarized key information from a shift.

At 2040, the ventilator report is displayed. For example, ventilator report is displayed on a ventilator.

Suggesting Ventilator Protocols

Figure 21:
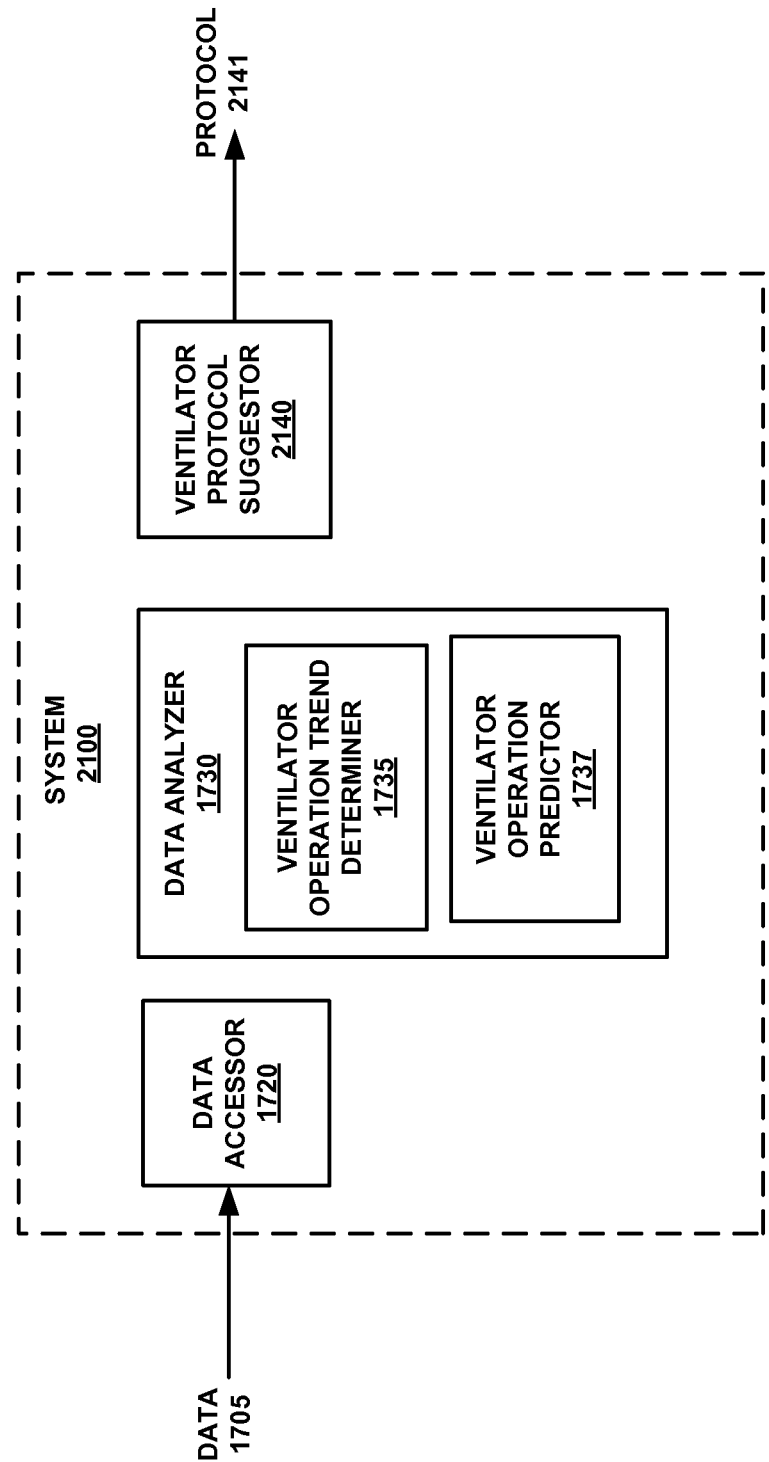

FIG. 21 depicts an embodiment of system 2100 for suggesting ventilator protocols. It should be appreciated that system 2100 is similar to system 1700, however, system 2100 includes ventilator protocol suggestor 2140 configured for suggesting protocol 2141. Ventilator protocol suggestor 2140 generates protocol 2141 for a ventilator based on the analyzed aggregated data.

In general, system 2100 receives patient information such as symptoms, medication, age, sex, weight. Accordingly, ventilator protocol suggestor 2140 suggests a protocol based on clinician based provided diagnostic information and a comparison of the patient information to aggregated ventilation outcome information.

Protocol 2141 may be a variety of different protocols, such as, but not limited to, weaning, sedation, neonatal, O2 settings, etc. In one embodiment, protocol 2141 is customizable. In various embodiments, protocol 2141 can be displayed on a display screen of a ventilator and/or forwarded to a hand-held interface or other network device.

Figure 22:
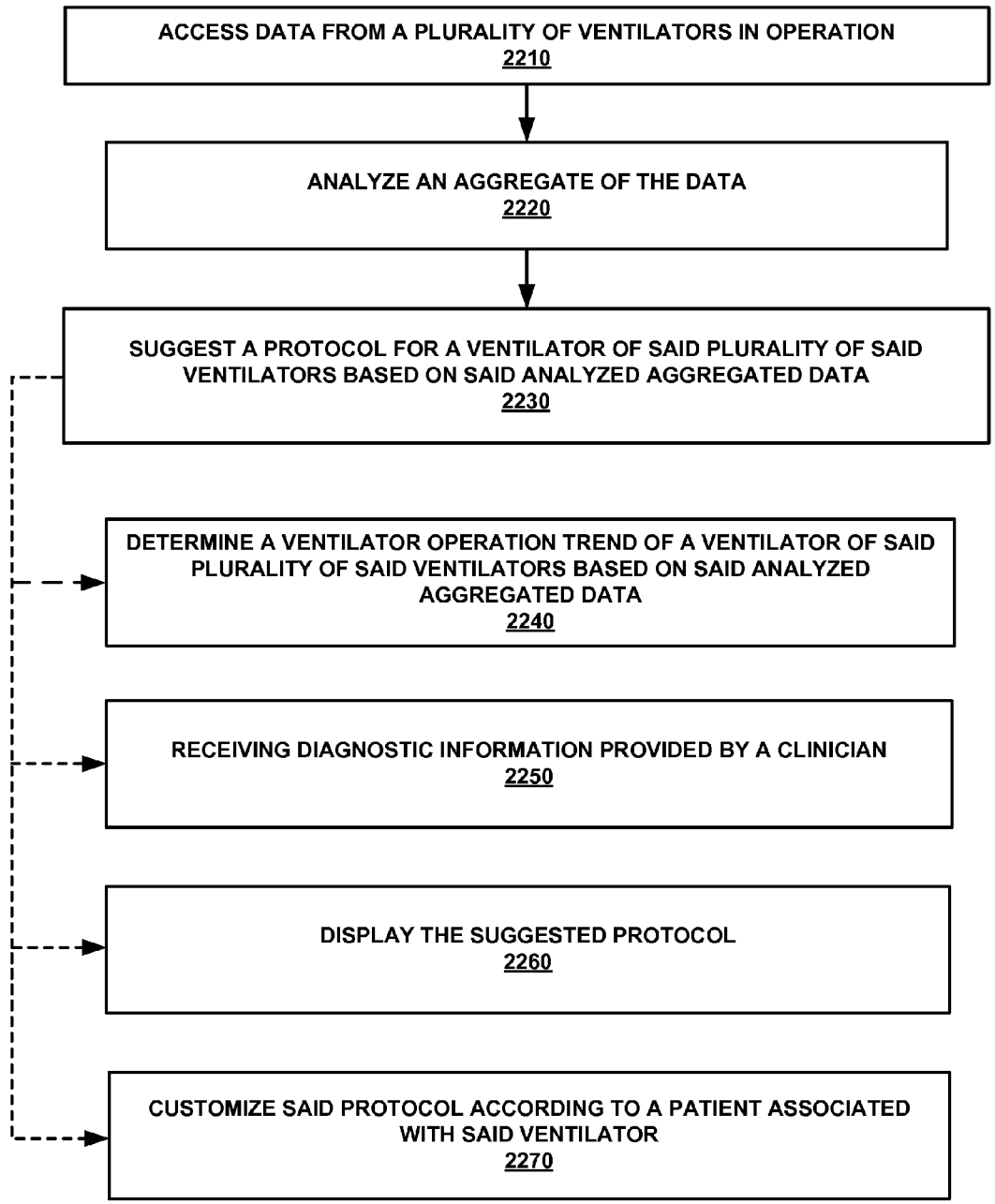
FIG. 22 illustrates an embodiment a method for suggesting ventilator protocols.

FIG. 22 depicts an embodiment of a method 2200 for suggesting ventilator protocols. In various embodiments, method 2200 is carried out by processors and electrical components under the control of computer readable and computer executable instructions. The computer readable and computer executable instructions reside, for example, in a data storage medium such as computer usable volatile and non-volatile memory. However, the computer readable and computer executable instructions may reside in any type of computer readable storage medium. In some embodiments, method 2200 is performed at least by system 2100, as depicted in FIG. 21.

At 2210 of method 2200, data is accessed from a plurality of ventilators in operation. At 2220, an aggregate of the data is analyzed.

At 2230, a protocol for a ventilator is suggested based on the analyzed aggregated data. For example, ventilator protocol suggestor 2140 suggests protocol 2141 for a ventilator.

At 2240, a ventilator operation trend is determined based on the analyzed aggregated data.

At 2250, diagnostic information provided by a clinician is received. For example, data accessor 1720 receives data 1705, which includes diagnostic information provided by a clinician.

At 2260, the protocol is displayed. For example, protocol 2141 is displayed on a display of a ventilator.

At 2270, the protocol is customized according to a patient associated with the ventilator. For example, protocol 2141 is customized according to a patient associated with ventilator 1750.

Ventilation Harm Index

Figure 23:
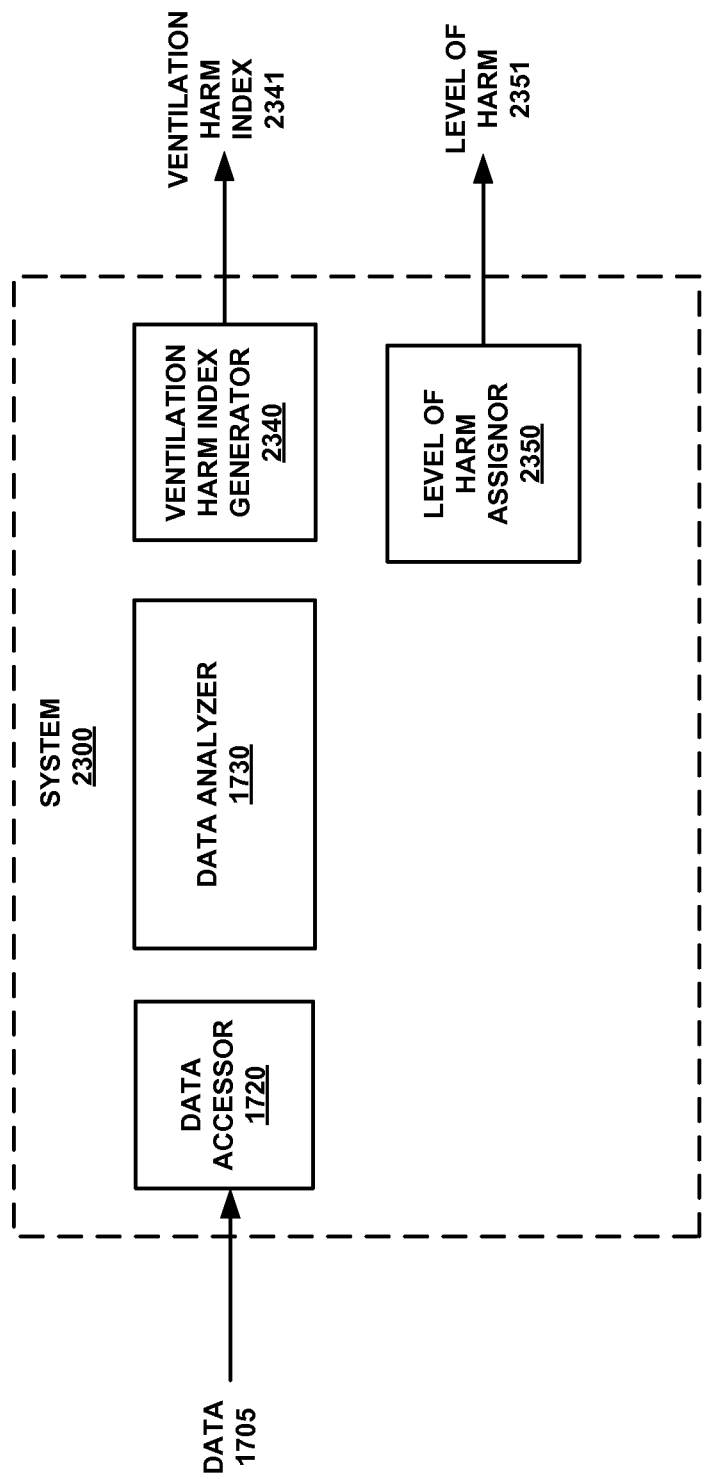

FIG. 23 depicts an embodiment of system 2300 for generating a ventilation harm index. It should be appreciated that system 2300 is similar to system 1700, however, system 2300 includes ventilation harm index generator 2340 and level of harm assignor 2350.

Ventilation harm index generator 2340 generates ventilation harm index 2341 based on the analyzed aggregated data or outcomes from the plurality of ventilators. In various embodiments, ventilator harm index 2341 can be viewed on the hosted or deployed knowledge portal.

Level of harm assignor 2350 is configured for assigning a level of harm 2351 to a ventilator setting. Typically, a ventilator is able to perform a plurality of operations that are adjusted or controlled by ventilator settings. The ventilator settings may include time of ventilation at various levels, level of oxygen, etc.

During use, when a clinician attempts to set or adjust the operation of the ventilator by inputting a ventilator setting, a level of harm 2351 is assigned to the attempted input or change of ventilator setting.

The level of harm 2351 is displayed or presented to the clinician in response to the attempted input or change of ventilator setting. In various embodiments, the level of harm 2351 includes a degradation of low, medium or high level of harm. It should be appreciated that the level of harm may have other degradations.

In one embodiment, there may be a delayed implementation of the ventilator setting (e.g., three seconds) to allow the clinician to cancel the ventilator setting because the level of harm assigned to the setting was high.

In another embodiment, the clinician may be presented with the level of harm and then required to verify the setting. In such an embodiment, the verification may be required for certain levels of harm.

In a further embodiment, for certain harm index levels, only certain personnel may be allowed to initiate the setting/adjustment of the ventilator. This could be assured by some form of clinician ID, logon etc.

Figure 24:
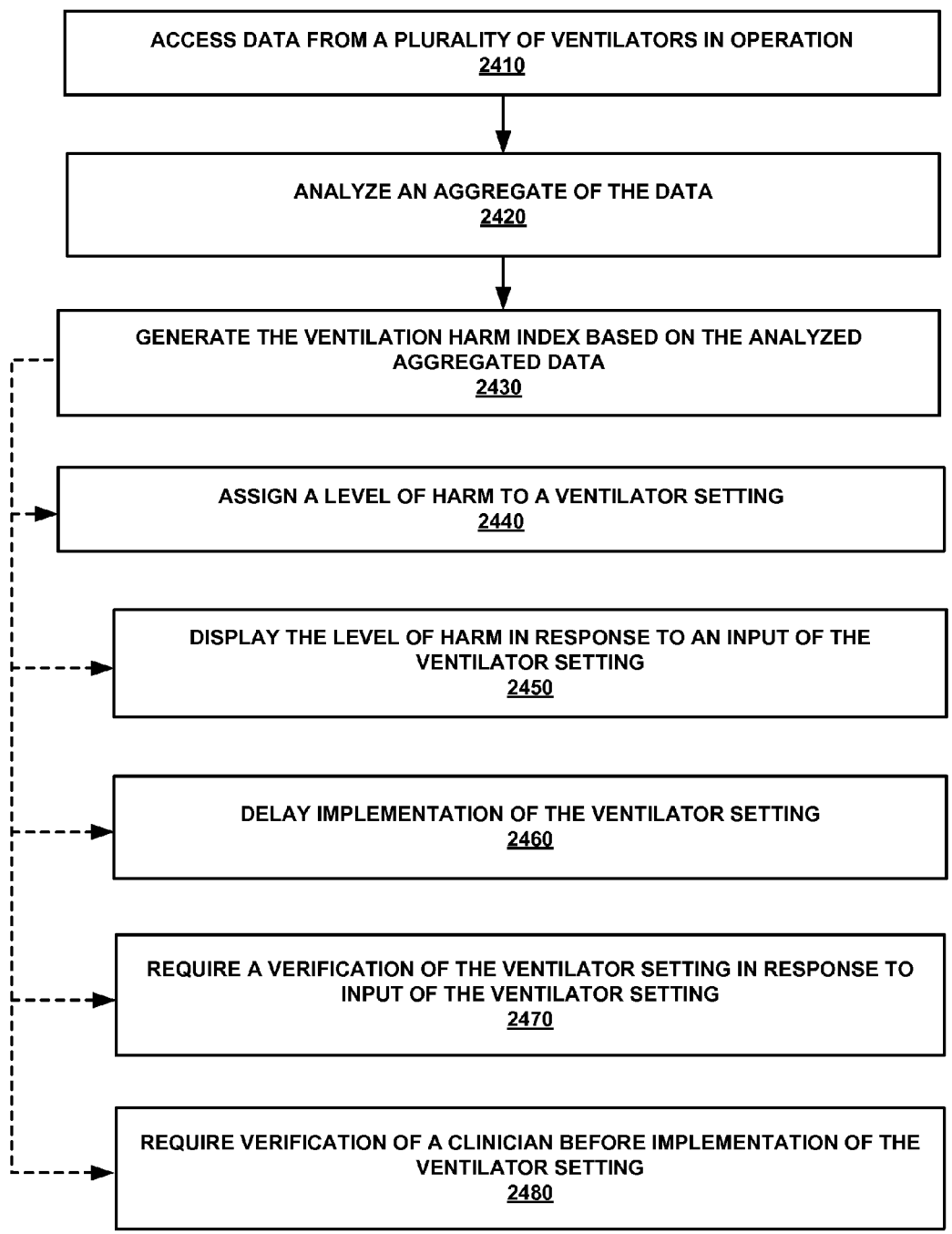
FIG. 24 illustrates an embodiment of a method for generating a ventilation harm index.

FIG. 24 depicts an embodiment of a method 2400 for generating a ventilation harm index. In various embodiments, method 2400 is carried out by processors and electrical components under the control of computer readable and computer executable instructions. The computer readable and computer executable instructions reside, for example, in a data storage medium such as computer usable volatile and non-volatile memory. However, the computer readable and computer executable instructions may reside in any type of computer readable storage medium. In some embodiments, method 2400 is performed at least by system 2300, as depicted in FIG. 23.

At 2410 of method 2400, data is accessed from a plurality of ventilators in operation. At 2420, an aggregate of the data is analyzed.

At 2430, the ventilation harm index is generated based on the analyzed aggregated data. For example, ventilation harm index generator 2340 generates ventilation harm index 2341.

At 2440, a level of harm is assigned to a ventilator setting. For example, a high level of harm is assigned to a certain level of oxygen setting.

At 2450, the level of harm is displayed in response to an input of the ventilator setting. For example, a clinician adjusts the level of oxygen setting and the level of harm is displayed in response to the adjustment.

At 2460, implementation of the ventilator setting is delayed. For example, the level of oxygen is substantially increased, as a result, the implementation of the increased level of oxygen is delayed such that the clinician can correctly adjust the level of oxygen.

At 2470, a verification of the ventilator setting is required in response to input of the ventilator setting. For example, the level of oxygen is substantially increased, as a result, a verification of the ventilator setting is require to ensure that the level of oxygen change is correct.

At 2480, verification of a clinician is required before implementation of the ventilator setting. For example, certain ventilator settings are only allowed by certain verified clinicians.

Ventilator Avoidance Report

Figure 25:
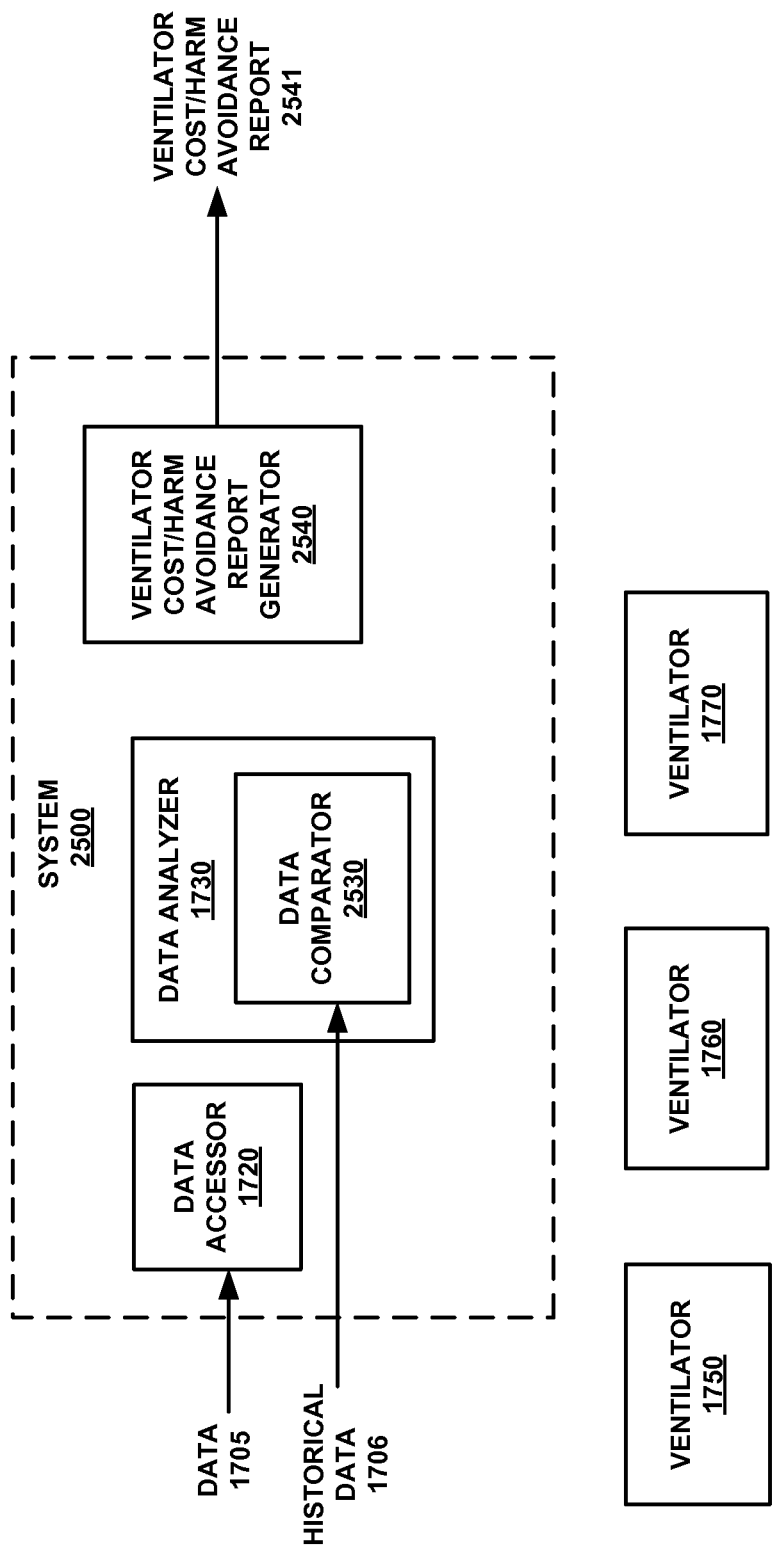

FIG. 25 depicts an embodiment of system 2500 for generating a ventilator avoidance report. In one embodiment, system 2500 is similar to system 1700, however, system 2500 includes data comparator 2530 and a report generator (e.g., cost/harm avoidance report generator 2540) configured to generate a ventilator avoidance report (e.g., ventilator cost/harm avoidance report 2541).

During use of system 2500, data accessor 1720 accesses data 1705 from a ventilator (e.g., ventilator 1750) during operation. Data 1705 may be any operation data from the ventilator. For example, data 1705 may be associated with any protocol and/or customizable protocol.

Data comparator 2530 compares data 1705 with historical data 1706. Historical data 1706 is any operational data associated with one or more other ventilators. For example, historical data 1706 can be empirical data, rules of thumb, protocols, operational history, etc. In various embodiments, historical data 1706 can also include hospital costs, such as, reimbursement, cost to ventilate a patient, labor expenses, etc.

Ventilator 1750 may be similar to the other ventilators (e.g., ventilator 1760 and 1770). However, ventilator 1750 is distinguished or different than the other ventilators in some way. For example, ventilator 1750 may be an upgraded version of ventilator 1760 and/or 1770.

Data comparator 2530 compares data 1705 with associated historical data from at least one other ventilator. For example, data comparator compares operation data of ventilator 1750 with historical operation data from another ventilator. In such an example, data comparator 2530 compares the results of protocols related to oxygen levels of ventilator 1750 with results of protocols related to oxygen levels of other ventilators.

Accordingly, report generator 2540 generates ventilator avoidance report 2541 based on the comparison of data comparator 2530. The ventilator avoidance report can describe the costs and/or harm that are avoided by utilizing ventilator 1750 rather than ventilators 1760 and/or 1770. The avoidance of costs can describe the amount of money saved, hospitalization days saved, etc. Moreover, because hospital beds may be scarce commodities, the report can help make the case for the use of ventilator 1750 rather than ventilators 1760 and/or 1770.

The ventilator avoidance report can capture or record harms avoided based on a variety of factors, such as, shorter hospitalization, faster weaning (versus a basic ventilator), number of times that ventilator rules prevented danger to a patient and what the likely outcome would have been (e.g., additional hospitalization, longer ventilation, death, etc.). As a result, the report helps make the case for the benefits of ventilator 1750 versus basic ventilators (e.g., ventilators 1760 and/or 1770) by preventing harms (which would also save money). In one embodiment, ventilator avoidance report 2541 describes how much money was saved by getting the patient off of the ventilator sooner versus a basic ventilator.

Figure 26:
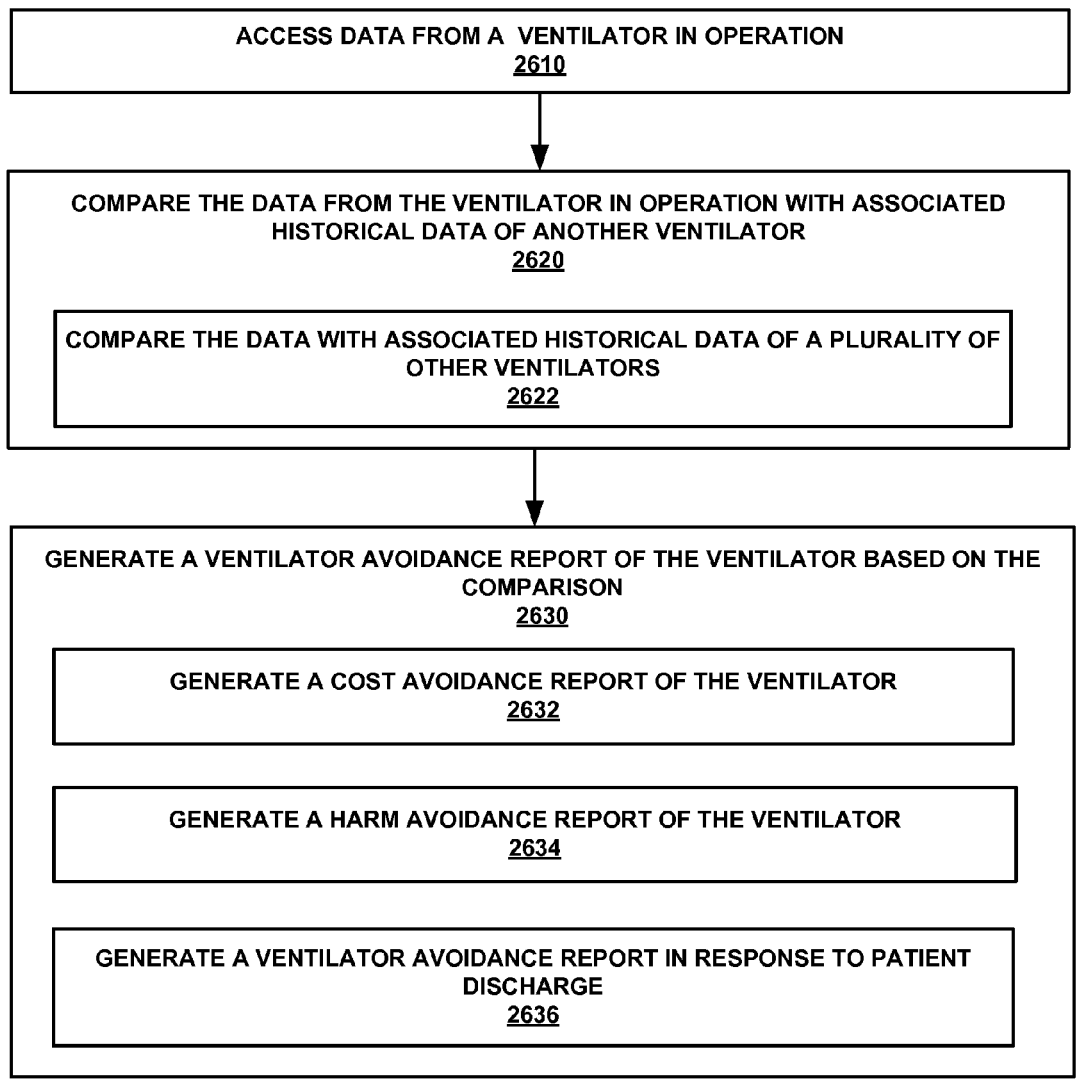
FIG. 26 illustrates an embodiment of a method for generating a ventilator avoidance report.

FIG. 26 depicts an embodiment of a method 2600 for generating a ventilator avoidance report. In various embodiments, method 2600 is carried out by processors and electrical components under the control of computer readable and computer executable instructions. The computer readable and computer executable instructions reside, for example, in a data storage medium such as computer usable volatile and non-volatile memory. However, the computer readable and computer executable instructions may reside in any type of computer readable storage medium. In some embodiments, method 2600 is performed at least by system 2500, as depicted in FIG. 25.

At 2610 of method 2600, data is accessed from a ventilator in operation. For example, data 1705 is accessed from ventilator 1750 by data accessor 1720.

At 2620, the data from the ventilator in operation is compared with associated historical data of another ventilator. For example, data 1705 (e.g., oxygen level data) of ventilator 1750 is compared with associated historical data 1706 (e.g., oxygen level data) of ventilator 1760.

In one embodiment, at 2622, the data is compared with associated historical data of a plurality of other ventilators. For example, data 1705 (e.g., oxygen level data) of ventilator 1750 is compared with associated historical data 1706 (e.g., oxygen level data) of ventilators 1760 and 1770.

At 2630, a ventilator avoidance report of the ventilator is generated based on the comparison. For example, report generator 2540 generates avoidance report 2541 based on the comparison by data comparator 2530.

In one embodiment, at 2632, a cost avoidance report is generated. In another embodiment, at 2634, a harm avoidance report is generated. In a further embodiment, a ventilator avoidance report is generated in response to a patient being discharged from the hospital or having the ventilation services end.

Assisting Ventilator Documentation at a Point of Care

Typically, ventilator documentation is executed manually by a clinician and/or executed at a computer system that is in another location than the point of care (e.g., immediate location of ventilator and/or patient). Accordingly, the work flow of ventilator documentation is inefficient. Moreover, human error, such as incorrect transcribing, may occur.

Figure 27:
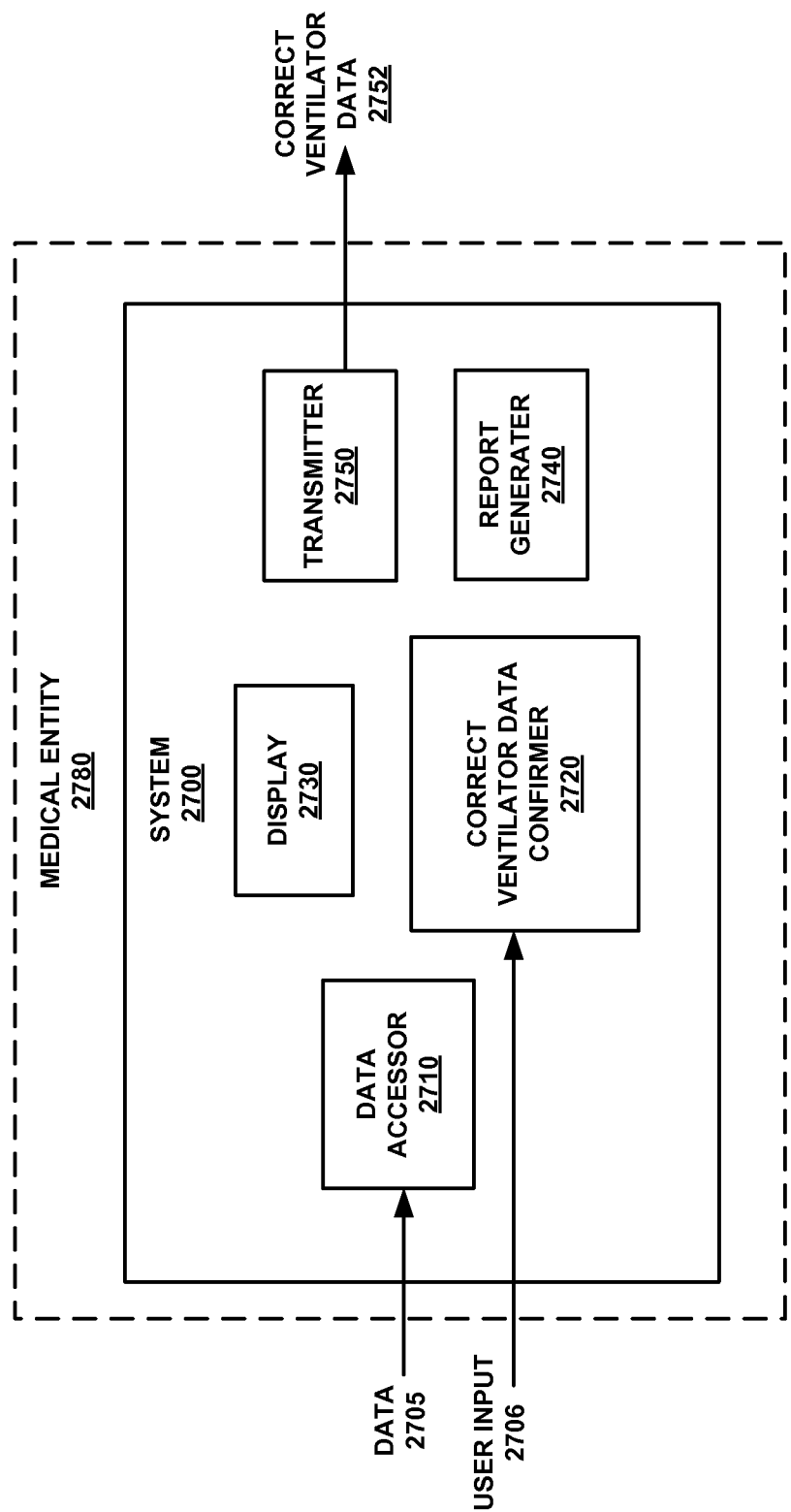

FIG. 27 depicts an embodiment of system 2700 for assisting ventilator documentation at a point of care. In general, system 2700 facilitates in a more efficient, accurate, and/or timely method of documentation at a point of care.

System 2700 includes data accessor 2710, correct ventilator data confirmer 2720, display 2730, report generator 2740, and transmitter 2750.

Data accessor 2710 is configured to access data 2705. Data 2705 can be any ventilator data associated with a ventilator. For example, data 2705 is streaming (full) ventilator data or a snapshot of ventilator data that can be annotated for the rounds with patient vitals (e.g., breath sounds) and observations (e.g., patient orientation, rescue equipment is near point of care).

Data 2705 can also include any information that facilitates in ventilator documentation. For example, data 2705 can include ventilator parameters, medication treatment (e.g., assess breathing before and after treatment), ventilator changes, weaning, etc.

Data 2705 can be accessed directly from the ventilator or can be accessed from a medical entity such as a healthcare facility network, knowledge portal, etc. In one embodiment, data 2705 includes any data associated with any another medical device that is associated with the ventilator and/or patient.

Data 2705 is displayed on display 2730. For example, data 2705 is pre-populated into a ventilator documentation format.

Correct ventilator data confirmer 2720 is configured for confirming that ventilator data is correct at point of care based on user input. For example, data 2705 is displayed on display 2730 for viewing by a clinician. The data is used to generate ventilation documentation. The clinician reviews and signs off that the ventilation documentation is correct and thereby confirms whether or not that ventilation documentation is correct.

The confirmed correct ventilation documentation at the point of care improves the accuracy of the ventilation documentation. The accuracy is improved because, but not limited to, transcribing is not required, and the ventilation documentation information is prepopulated and the clinician verifies the documentation, if correct, at the point of care.

Transmitter 2750 is configured to transmit correct ventilator data 2752 (e.g., signed off ventilation documentation). In one embodiment, correct ventilator data 2752 is transmitted to a patient medical record, for example, in EMAR formant (e.g., level 7 compatible interface).

Report generator 2740 is configured to generate reports based on correct ventilator data 2752. In one embodiment, report generator 2740 generates a round report based on correct ventilator data 2752.

In one embodiment, system 2700 is disposed or integrated in medical entity 2780. In one embodiment, medical entity 2780 is a ventilator.

In another embodiment, medical entity 2780 is a handheld device (e.g., handheld computer, tablet, PDA, etc.). In such an embodiment, the handheld device can wirelessly communicate with a ventilator over WiFi, short range wireless, WPAN, or cellular network.

System 2700 can also be utilized for caregiver verification for login/access to a ventilator (e.g., ventilator 110, ventilator 710, etc.). The verification may be authorized by a caregiver identifier obtained by a card, barcode, biometric means, etc.

Figure 28:
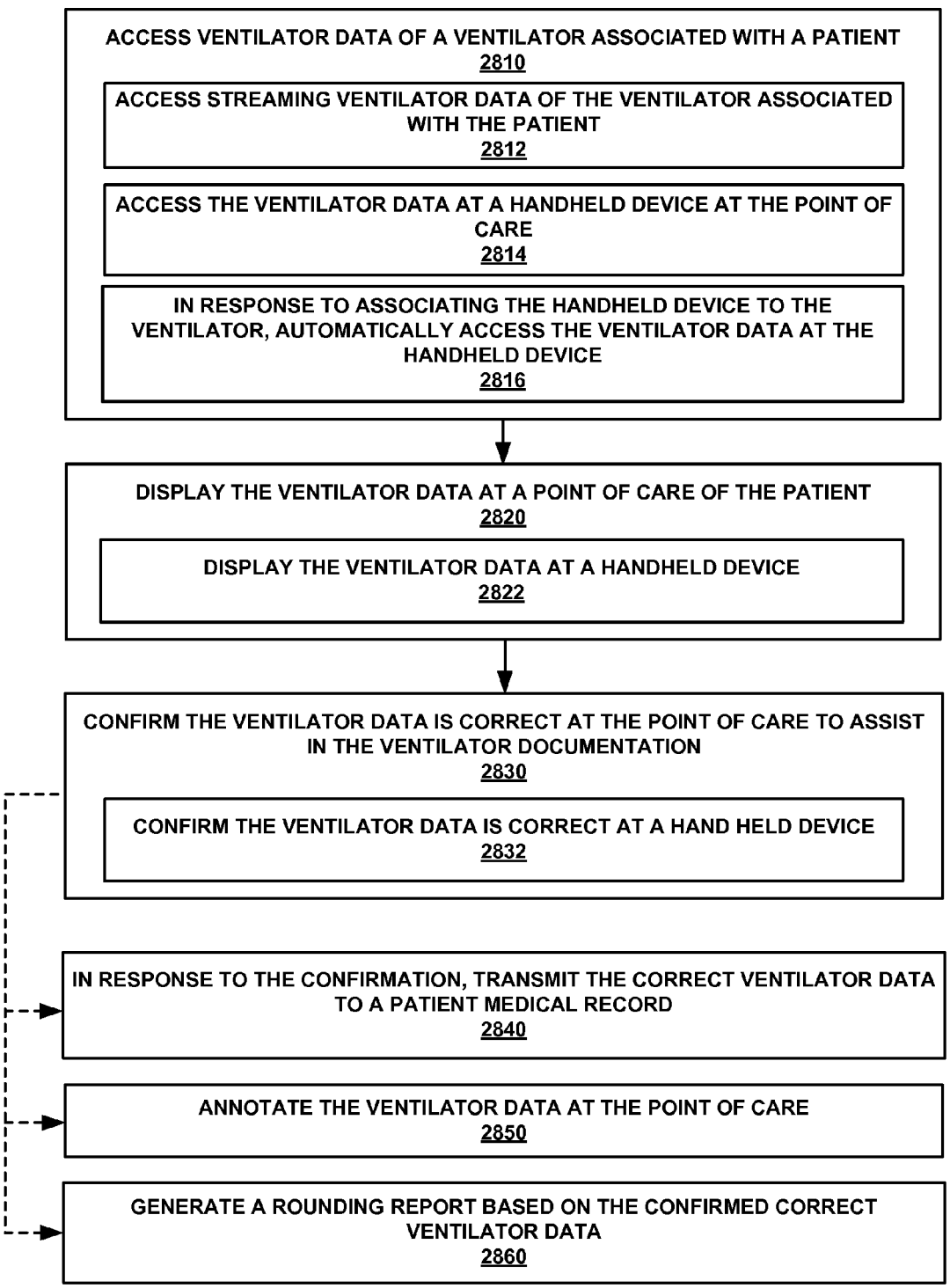
FIG. 28 illustrates an embodiment of a method for assisting ventilator documentation at a point of care.

FIG. 28 depicts an embodiment of a method 2800 for assisting in ventilator documentation at a point of care. In various embodiments, method 2800 is carried out by processors and electrical components under the control of computer readable and computer executable instructions. The computer readable and computer executable instructions reside, for example, in a data storage medium such as computer usable volatile and non-volatile memory. However, the computer readable and computer executable instructions may reside in any type of computer readable storage medium. In some embodiments, method 2800 is performed at least by system 2700, as depicted in FIG. 27.

At 2810, ventilator data of a ventilator associated with a patient is accessed. For example, data 2705 that is associated with a ventilator and a patient is accessed by data accessor 2710.

In one embodiment, at 2812, streaming ventilator data of ventilator associated with the patient is accessed. For example, data accessor 2710 accesses or captures streaming (full) ventilator data from the ventilator. In other words, data accessor 2710 captures data 2705 which is in real-time.

In another embodiment, at 2814, the ventilator data is accessed at a handheld device at the point of care. For example, system 2700 is implemented in a handheld device. Therefore, data 2705 is accessed at the handheld device at the point of care.

In a further embodiment, at 2816, in response to associating the handheld device to the ventilator, the ventilator data at the handheld device is automatically accessed. For example, a handheld device (including system 2700) is associated with the ventilator, for example, by scanning a barcode on the ventilator. As a result the handheld device is synced to the ventilator. In response to the association, all available vitals are automatically accessed and coupled to the handheld device.

At 2820, the ventilator data is displayed at a point of care of the patient. For example, a ventilator (including system 2700) displays data 2705 on display 2730.

In one embodiment, at 2832, the ventilator data is displayed at the point of care on a handheld device. For example, a handheld device associated with a clinician displays data 2705 on display 2730.

At 2830, the ventilator data is confirmed to be correct at the point of care to assist in the ventilator documentation. For example, a clinician reviews data 2705 that is utilized to form ventilator documentation. If the displayed data is correct for proper ventilator documentation, then the clinician confirms the propriety of the ventilator documentation by generating user input 2706.

In one embodiment, at 2832, the ventilator data is confirmed to be correct at a hand held device. For example, the clinician confirms the propriety of the ventilator documentation by generating user input 2706 at the handheld device.

At 2840, in response to the confirmation, transmit the correct ventilator data to a patient medical record. For example, transmitter 2750 transmits correct ventilator data 2752 corresponding to a proper and correct ventilator documentation to a patient medical record.

At 2850, the ventilator data is annotated at the point of care. For example, data 2705 displayed on display 2730 is annotated by a clinician. In such an example, the clinician annotates or inputs data about weaning, change of ventilator, etc.

At 2860, a rounding report based on the confirmed correct ventilator data is generated. For example, report generator 2740 generates a rounding report based on correct ventilator data 2752.

Embodiment of a System

Figure 29:
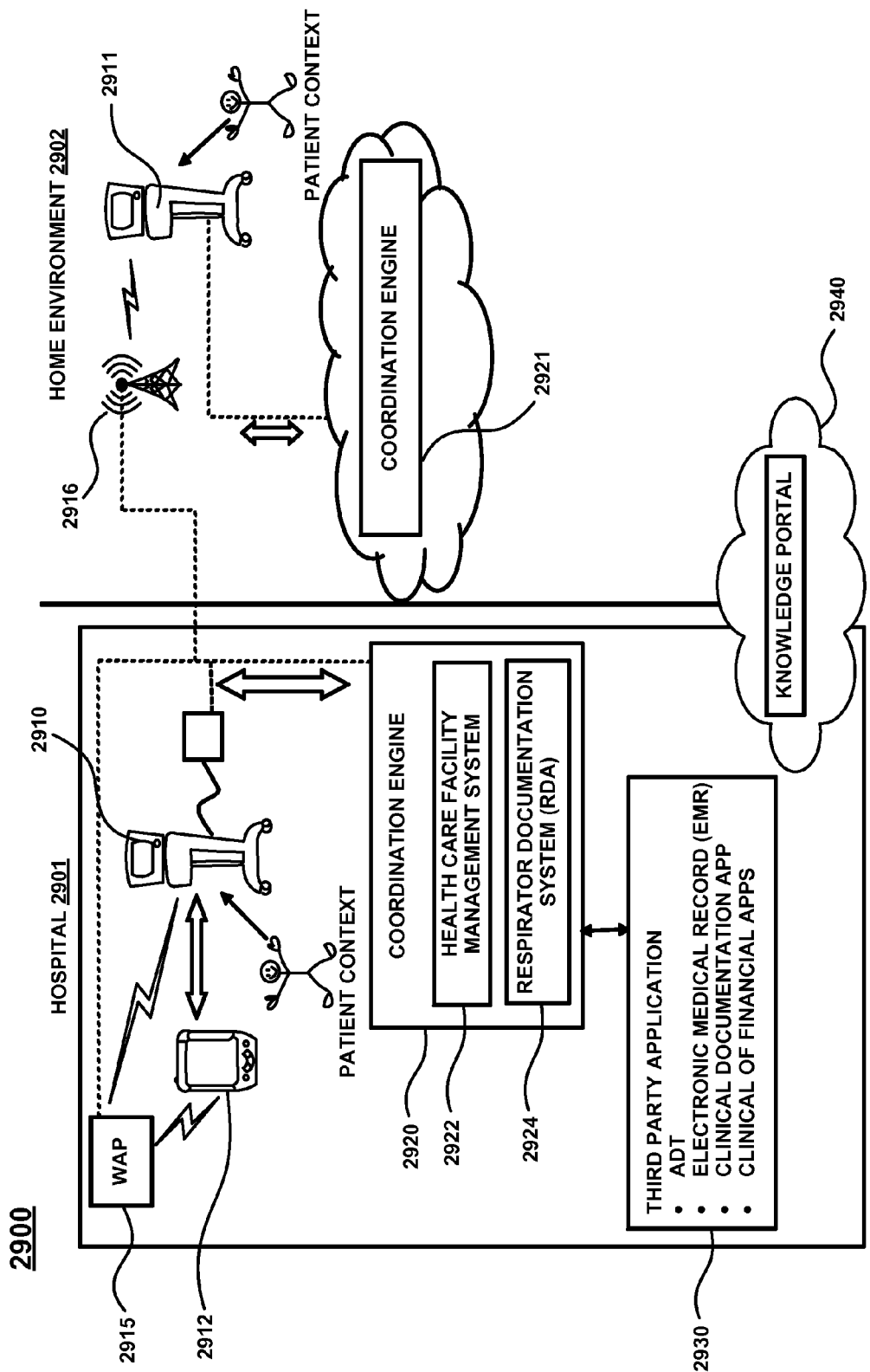

FIG. 29 depicts an embodiment of a medical system 2900. In various embodiments, medical system 2900 includes variations and combinations of devices, systems, methods described in detail above.

Medical system 2900 includes a hospital 2901 and/or home environment 2902.

In one embodiment, hospital 2901 includes ventilator 2910 (e.g., ventilator 110, ventilator 710, etc.) that bi-directionally communicates with medical entities in a network (e.g., WAN). For example, ventilator 2910 bi-directionally communicates with coordination engine 2920, third party application 2930, knowledge portal 2940, handheld device 2912, etc. Ventilator 2910 can wirelessly connect to the network via WAP 2915 or a wireline.

In one embodiment, home environment 2902 includes ventilator 2911 (e.g., ventilator 110, ventilator 710, etc.) that bi-directionally communicates with medical entities. For example, ventilator 2911 bi-directionally communicates with medical entities in the network of hospital 2901 (as described above) via cellular network 2916 and/or with coordination engine 2921.

In one embodiment, system 2900 allows for contextualizing ventilator data (e.g., patient context) for ventilators 2910 and 2911, as described above with respect to FIGS. 4-6.

Coordination engine 2920 and 2921 are an interface for third party applications (e.g., third party applications 2930). For example, ventilator 2910 may access ADT information from a third party ADT via coordination engine 2920. It should be appreciated that the coordination engines can be integrated in a single location, such as a server, or can be distributed across various computer devices/systems.

Third party applications 2930 can include, but are not limited to, an ADT application, electronic medical record (EMR) application, clinical documentation application, various clinical or financial applications, etc.

In various embodiments, ventilators 2910 and/or 2911 may bi-directionally communicate with various applications associated with coordination engine 2920 (or coordination engine 2921). For example, ventilator 2910 bi-directionally communicates with healthcare facility management system 2922.

In another embodiment, ventilator 2910 bi-directionally communicates with respiratory documentation system or application (RDA) 2924. It should be appreciated that the RDA can also run on other medical devices such as handheld device 2912.

In various embodiments, the ventilators are capable of ventilator data logging. For example, ventilator 2911 may be offline, however, it is still able to capture and store data. Once the ventilator comes back online the stored data is transmitted to medical entities such as coordination engine 2921.

Various embodiments of the present invention are thus described. It should be appreciated that embodiments, as described herein, can be utilized or implemented alone or in combination with one another. While the present invention has been described in particular embodiments, it should be appreciated that the present invention should not be construed as limited by such embodiments, but rather construed according to the following claims.

The invention claimed is:

1. A method for prompting a caregiver using a ventilation harm index about potential harm to a patient by implementation of a ventilator setting on a ventilator, said method comprising:
   accessing data from a plurality of ventilators in operation;
   generating said ventilation harm index based on an analysis of an aggregate of said data, wherein said ventilation harm index comprises a plurality of harm levels indicative of different levels of harm that are expected to occur;
   assigning at least one of the plurality of harm levels to the ventilator setting of the ventilator, wherein the at least one of the plurality of harm levels assigned to the ventilator setting is indicative of a level of harm that is expected to occur to a patient associated with the ventilator when operating the ventilator at the ventilator setting;
   receiving a selection of the ventilator setting comprising the assigned at least one of the plurality of harm levels;
   determining, based on the at least one of the plurality of harm levels assigned to the selected ventilator setting, whether either a verification of the selection of the ventilator setting by a user is required, or a delay of implementation of the ventilator setting is required;
   when the determination indicates that the verification, based on the at least one of the plurality of harm levels assigned to the selected ventilator setting, is required, then prompting the user for verification of the selection of the ventilator setting, the prompt comprising an indicator of the at least one of the plurality of harm levels assigned to the selected ventilator setting and receiving a verification of the selection of the ventilator setting from the user;
   when the determination indicates that the delay, based on the at least one of the plurality of harm levels assigned to the selected ventilator setting, is required, then delaying implementation of said ventilator setting for a preset duration of time in order to permit the user to cancel implementation of said ventilator setting during the preset duration of time;
   implementing the selected ventilator setting on the ventilator upon receiving the verification of the selection of the ventilator setting from the user when the determination indicates that the verification is required; and
   implementing the selected ventilator setting on the ventilator after the preset duration of time has passed and when the user does not cancel implementation of said ventilator setting during the preset duration of time when the determination indicates that the delay is required.

2. The method of claim 1, wherein said ventilator setting comprises a time of ventilation or a level of oxygen.

3. The method of claim 1, wherein receiving the verification of the selection of the ventilator setting from the user comprises determining whether the user has authorization to verify the selection of the ventilator setting, and wherein implementing the selected ventilator setting upon receiving the verification of the selection of the ventilator setting from the user comprises implementing the selected ventilator when the determination indicates the user has authorization to verify the selection of the ventilator setting.

4. The method of claim 1,
   wherein the plurality of harm levels comprise a low level of harm and a high level of harm, and
   wherein the assigned at least one of the plurality of harm levels to the ventilator setting of the ventilator comprises a high level of harm, and
   wherein the implementation of said ventilator setting is delayed for a preset duration of time because the assigned at least one of the plurality of harm levels to the ventilator setting of the ventilator comprises a high level of harm.

5. The method of claim 1, wherein at least one of the plurality of harm levels for the patient is assigned to each of a plurality of ventilator settings of the ventilator.

6. A system for prompting a caregiver using a ventilation harm index about potential harm to a patient by implementation of a ventilator setting on a ventilator, comprising:
- a memory comprising instructions; and
- a processor configured to execute the instructions to:
  - access data from plurality of ventilators in operation;
  - generate said ventilation harm index based on an analysis of an aggregate of said data, wherein said ventilation harm index comprises a plurality of harm levels indicative of different levels of harm that are expected to occur;
  - assign at least one of the plurality of harm levels to the ventilator setting of the ventilator, wherein the at least one of the plurality of harm levels assigned to the ventilator setting is indicative of a level of harm that is expected to occur to a patient associated with the ventilator when operating the ventilator at the ventilator setting;
  - receive a selection of the ventilator setting comprising the assigned at least one of the plurality of harm levels;
  - determine, based on the at least one of the plurality of harm levels assigned to the selected ventilator setting, whether either a verification of the selection of the ventilator setting by a user is required, or a delay of implementation of the ventilator setting is required;
  - when the determination indicates that the verification, based on the at least one of the plurality of harm levels assigned to the selected ventilator setting, is required, then prompt the user for verification of the selection of the ventilator setting, the prompt comprising an indicator of the at least one of the plurality of harm levels assigned to the selected ventilator setting and receive a verification of the selection of the ventilator setting from the user;
  - when the determination indicates that the delay, based on the at least one of the plurality of harm levels assigned to the selected ventilator setting, is required, then delay implementation of said ventilator setting for a preset duration of time in order to permit the user to cancel implementation of said ventilator setting during the preset duration of time;
  - implement the selected ventilator setting on the ventilator upon receiving the verification of the selection of the ventilator setting from the user when the determination indicates that the verification is required; and
  - implement the selected ventilator setting on the ventilator after the preset duration of time has passed and when the user does not cancel implementation of said ventilator setting during the preset duration of time when the determination indicates that the delay is required.

7. The system of claim 6, wherein said ventilator setting comprises a time of ventilation or a level of oxygen.

8. The system of claim 6,
wherein the plurality of harm levels comprise a low level of harm and a high level of harm,
wherein the assigned at least one of the plurality of harm levels to the ventilator setting of the ventilator comprises a high level of harm, and
wherein the processor is configured to delay implementation of said ventilator setting for a preset duration of time because the assigned at least one of the plurality of harm levels to the ventilator setting of the ventilator comprises a high level of harm.

9. The system of claim 6, wherein receiving the verification of the selection of the ventilator setting from the user comprises determining whether the user has authorization to verify the selection of the ventilator setting, and wherein implementing the selected ventilator setting upon receiving the verification of the selection of the ventilator setting from the user comprises implementing the selected ventilator when the determination indicates the user has authorization to verify the selection of the ventilator setting.

10. The system of claim 6, wherein the processor is further configured to assign at least one of the plurality of harm levels for the patient to each of a plurality of ventilator settings of the ventilator.

11. A machine-readable storage medium comprising machine-readable instructions for causing a processor to execute a method for prompting a caregiver using a ventilation harm index about potential harm to a patient by implementation of a ventilator setting on a ventilator, said method comprising:
- accessing data from a plurality of ventilators in operation;
- generating said ventilation harm index based on an analysis of an aggregate of data, wherein said ventilation harm index comprises a plurality of harm levels indicative of different levels of harm that are expected to occur;
- assigning at least one of the plurality of harm levels to the ventilator setting of the ventilator, wherein the at least one of the plurality of harm levels assigned to the ventilator setting is indicative of a level of harm that is expected to occur to a patient associated with the ventilator when operating the ventilator at the ventilator setting
- receiving a selection of the ventilator setting comprising the assigned at least one of the plurality of harm levels;
- determining, based on the at least one of the plurality of harm levels assigned to the selected ventilator setting, whether either a verification of the selection of the ventilator setting by a user is required, or a delay of implementation of the ventilator setting is required;
- when the determination indicates that the verification, based on the at least one of the plurality of harm levels assigned to the selected ventilator setting, is required, then prompting the user for verification of the selection of the ventilator setting, the prompt comprising an indicator of the at least one of the plurality of harm levels assigned to the selected ventilator setting and receiving a verification of the selection of the ventilator setting from the user;
- determining, based on the at least one of the plurality of harm levels assigned to the selected ventilator setting, whether the user has authorization to verify the selection of the ventilator setting;
- identifying an authorization level of the user;
- when the determination indicates that the delay, based on the at least one of the plurality of harm levels assigned to the selected ventilator setting, is required, then delay implementation of said ventilator setting for a preset duration of time in order to permit the user to cancel implementation of said ventilator setting during the preset duration of time when the identification of the authorization level of the user indicates the user has authorization;
- implementing the selected ventilator setting on the ventilator upon receiving the verification of the selection of the ventilator setting from the user when the determination indicates that the verification is required; and implementing the selected ventilator setting on the ventilator after the preset duration of time has passed and when the user does not cancel implementation of said ventilator setting during the preset duration of time when the determination indicates that the delay is required.

* * * * *